United States Patent
Henton et al.

(10) Patent No.: US 10,392,358 B2
(45) Date of Patent: Aug. 27, 2019

(54) OXIDATION CHEMISTRY ON FURAN ALDEHYDES

(71) Applicant: Micromidas, Inc., West Sacramento, CA (US)

(72) Inventors: Daniel R. Henton, Midland, MI (US); Makoto Nathanael Masuno, West Sacramento, CA (US); Ryan L. Smith, West Sacramento, CA (US); Alex B. Wood, West Sacramento, CA (US); Dimitri A. Hirsch-Weil, West Sacramento, CA (US); Christian T. Goralski, Midland, MI (US); Robert Joseph Araiza, West Sacramento, CA (US)

(73) Assignee: Micromidas, Inc., West Sacramento, CA (US)

( * ) Notice: Subject to any disclaimer, the term of this patent is extended or adjusted under 35 U.S.C. 154(b) by 0 days.

(21) Appl. No.: 15/760,949

(22) PCT Filed: Sep. 16, 2016

(86) PCT No.: PCT/US2016/052315
§ 371 (c)(1),
(2) Date: Mar. 16, 2018

(87) PCT Pub. No.: WO2017/049211
PCT Pub. Date: Mar. 23, 2017

(65) Prior Publication Data
US 2018/0265488 A1    Sep. 20, 2018

Related U.S. Application Data

(60) Provisional application No. 62/220,181, filed on Sep. 17, 2015.

(51) Int. Cl.
*C07D 307/02* (2006.01)
*C07D 307/54* (2006.01)
*B01J 19/00* (2006.01)

(52) U.S. Cl.
CPC ........ *C07D 307/54* (2013.01); *B01J 19/0006* (2013.01); *B01J 2219/00177* (2013.01)

(58) Field of Classification Search
CPC ................ C07D 307/54; B01J 19/0006; B01J 2219/00177
(Continued)

(56) References Cited

U.S. PATENT DOCUMENTS 2,450,108 A    9/1948   Bremner et al.
2,541,408 A    2/1951   Cockerille
(Continued)

FOREIGN PATENT DOCUMENTS

DE    4033563 A1    4/1992
FR    3008409 A1    1/2015
(Continued)

OTHER PUBLICATIONS

Andrisano et al., "Chloromethylations in the Furan Series. I. Alkyl 5-Alkoxymethyl- and 5-Arylaminomethyl-2-Furoates", Annali Di Chimica, vol. 40, 1950, pp. 30-34 (Foreign Language Only). (See Communication under 37 CFR § 1.98(a) (3)).
(Continued)

*Primary Examiner* — Taylor V Oh
(74) *Attorney, Agent, or Firm* — Morrison & Foerster LLP

(57) ABSTRACT

Provided herein are methods of producing halomethylfuroic and acyloxymethylfuroic acid and ester compounds from furfural starting compounds. For example, 5-chloromethyl-2-furoic acid may be produced from 5-chloromethylfurfural, in the presence of various oxidants. Salts of the furoic acids may also be produced.

50 Claims, 3 Drawing Sheets

(58) Field of Classification Search
USPC .......................................................... 549/484
See application file for complete search history.

(56) References Cited

U.S. PATENT DOCUMENTS

| | | | |
|---|---|---|---|
| 4,424,390 A | 1/1984 | Hamada et al. | |
| 4,549,025 A | 10/1985 | Dalcanale et al. | |
| 5,486,525 A * | 1/1996 | Summers, Jr. ........ | C07D 403/10 |
| | | | 514/303 |
| 6,956,040 B2 | 10/2005 | Mehta et al. | |
| 7,411,078 B2 | 8/2008 | Miura et al. | |
| 2015/0051413 A1 | 2/2015 | Kim et al. | |

FOREIGN PATENT DOCUMENTS

| | | |
|---|---|---|
| GB | 588377 A | 5/1947 |
| SU | 1159921 A1 | 6/1985 |
| WO | 1991/11419 A1 | 8/1991 |
| WO | 2001/87830 A2 | 11/2001 |
| WO | 2004/014869 A2 | 2/2004 |
| WO | 2004/037804 A1 | 5/2004 |
| WO | 2007/043835 A1 | 4/2007 |
| WO | 2011/043661 A1 | 4/2011 |
| WO | 2013/033058 A1 | 3/2013 |
| WO | 2013/033081 A2 | 3/2013 |
| WO | 2015/060829 A1 | 4/2015 |
| WO | WO2015056270 * | 4/2015 |

OTHER PUBLICATIONS

Andrisano et al., "Hyperconjugation of the Methyl Group in the Furan Series. Ultraviolet Absorption Spectra of Some 1-Methylfurans", Gazzetta Chimica Italiana, vol. 80, 1950, pp. 730-740 (Foreign Language Only). (See Communication under 37 CFR § 1.98(a) (3)).
Andrisano, Renato, "Clorometilazione Nella Serie Furanica : Ulteriori Prodotti Dl Sostituzione Al Cloro Nel Residuo Clorometilico", Bologna Universita Facolta Di Chimica Industriale Bollettino Scientifico, vol. 8, 1950, pp. 17-18 (Foreign Language Only). (See Communication under 37 CFR § 1.98(a) (3)).
Anelli et al., "Fast and Selective Oxidation of Primary Alcohols to Aldehydes or to Carboxylic Acids and of Seconodary Alcohols to Ketones Mediated by Oxoammonium Salts under Two-Phase Conditions", The Journal of Organic Chemistry, vol. 52, No. 12, 1987, pp. 2559-2562.
Ardemani et al., "Solid Base Catalysed 5-HMF Oxidation to 2,5-FDCA Over Au/Hydrotalcites: Fact or Fiction?", Chem. Sci., vol. 6, 2015, pp. 4940-4945.
Brasholz et al., "Highly Efficient Dehydration of Carbohydrates to 5-(chloromethyl)Furfural(CMF), 5-(hydroxymethyl)Furfural (HMF) and Levulinic acid by Biphasic Continuous Flow Processing", Green Chemistry, vol. 13, 2011, pp. 1114-1117.
Cha et al., "Combined Biomass Valorization and Hydrogen Production in a Photoelectrochemical Cell", Nature Chemistry, vol. 7, Apr. 2015, pp. 328-333.
Coelho et al., "Trienamines derived from 5-Substituted Furfurals: Remote ε-Functionalization of 2,4-Dienals", Organic & Biomolecular Chemistry, vol. 12, 2014, pp. 9324-9328.
Dalcanale et al., "Selective Oxidation of Aldehydes to Carboxylic Acids with Sodium Chlorite-Hydrogen Peroxide", J. Org. Chem., vol. 51, No. 4, 1986, pp. 567-569.
Dijkman et al., "Enzyme-Catalyzed Oxidation of 5-Hydroxymethylfurfural to Furan 2,5-Dicarboxylic Acid", Angew. Chem., vol. 126, 2014, pp. 6633-6636.
Dutta et al., "Production of 5-(Chloromethyl)Furan-2-Carbonyl Chloride and Furan-2,5-Dicarbonyl Chloride from Biomass-derived 5-(Chloromethyl)Furfural (CMF)", Green Chemistry, 2015, 3 pages.
Dutta et al., "Production of 5-(Chloromethyl)Furan-2-Carbonyl Chloride and Furan-2,5-Dicarbonyl Chloride from Biomass-derived 5-(Chloromethyl)Furfural (CMF)", Green Chemistry, 2015, pp. S1-S21.

Ginsburg, David, "The Action of t-Butyl Hypochlorite on Organic Compounds. II. Aromatic Aldehydes1", J. Am. Chem. Soc., vol. 73, Feb. 1951, pp. 702-704.
Grill et al., "An Efficient and Practical System for the Catalytic Oxidation of Alcohols, Aldehydes, and α,β-Unsaturated Carboxylic Acids", The Journal of Organic Chemistry, vol. 71, 2006, pp. 9291-9296.
Hachihama et al., "Syntheses of Polyesters Containing Furan Ring", Technology Reports of the Osaka University, vol. 8, No. 333, 1958, pp. 475-480.
Hansen et al., "Cu Catalyzed Oxidation of 5-Hydroxymethylfurfural to 2,5-Diformylfuran and 2,5-Furandicarboxylic Acid under Benign Reaction Conditions", Applied Catalysis A: General, vol. 456, 2013, pp. 44-50.
International Preliminary Report on Patentability received for PCT Patent Application No. PCT/US2016/052315, dated Mar. 29, 2018, 6 pages.
International Search Report and Written Opinion received for PCT Patent Application No. PCT/US2016/052315, dated Dec. 7, 2016, 8 pages.
Kang et al., "From Lignocellulosic Biomass to Furans via 5-Acetoxymethylfurfural as an Alternative to 5-Hydroxymethylfurfural", ChemSusChem, vol. 8, No. 7, Apr. 13, 2015, 11 pages.
Khilya et al., "Alkylation of 7-Hydroxy-3-Furylchromone and 7-hydroxyisoflavone by heterocyclic Halo Derivatives", Khimiya Geterotsiklicheskikh Soedinenii, vol. 10, 1972, pp. 1321-1323 (Foreign Language Only). (See Communication under 37 CFR § 1.98(a) (3)).
Lewkowski, Jarosław, "Synthesis, Chemistry and Applications of 5-Hydroxymethylfurfural and Its Derivatives", Archive for Organic Chemistry, vol. 2001, No. 1, 2001, pp. 17-54.
Liu et al., "Aerobic Oxidation of 5-Hydroxymethylfurfural into 2,5-Furandicarboxylic Acid in Water under Mild Conditions", Green Chemistry, vol. 17, 2015, pp. 1610-1617.
Lutkova et al., "Obtaining 2,5-Furandicarboxylic Acid and its Dimethyl Ester from Furfural", Plasticheskie Massy, No. 4, 1960, pp. 56-57 (Foreign Language Only). (See Communication under 37 CFR § 1.98(a) (3)).
Moldenhauer et al., "Beiträge Zur Furanchemie I", Justus Liebigs Annalen der Chemie, vol. 580, 1953, pp. 169-190. (See Communication under 37 CFR § 1.98(a) (3)).
Nguyen et al., "A Metal-Free, High Nitrogen-Doped Nanoporous Graphitic Carbon Catalyst for an Effective Aerobic HMF-to-FDCA Conversion", Green Chemistry, vol. 18, No. 22, Nov. 21, 2016, pp. 5957-5961.
Pichler et al., "Ruthenium Supported on High-Surface-Area Zirconia as an Efficient Catalyst for the Base-Free Oxidation of 5-Hydroxymethylfurfural to 2,5-Furandicarboxylic Acid", ChemSusChem, vol. 11, 2018, pp. 2083-2090.
Raach et al., "Sodium Chlorite-Hydrogen Peroxide—A Mild and Selective Reagent for the Oxidation of Aldehydes to Carboxylic Acids", J. Prakt. Chem., vol. 342, No. 6, Jun. 2000, pp. 605-608.
Rao et al., "Oxidation of Biomass derived 5-Hydroxymethylfurfural using Heterogeneous and Electrochemical Catalysis", Catalysis Today, vol. 195, 2012, pp. 144-154.
Saha et al., "Aerobic Oxidation of 5-Hydroxylmethylfurfural with Homogeneous and Nanoparticulate Catalysts", Catalysis Science & Technology, vol. 2, 2012, pp. 79-81.
Shi et al., "Oxidation of Benzyl Chlorides and Bromides to Benzoic Acids with 30% Hydrogen Peroxide in the Presence of Na2WO4, Na2VO4, or Na2MoO4 under Organic Solvent-Free Conditions", J. Org. Chem., vol. 66, No. 9, 2001, pp. 3235-3237.
Taniyama et al., "Identification of Furan Derivatives and Aliphatic Dibasic Acids by Paper Chromatography", The Journal of the Chemical Society of Japan, Industrial Chemisty Section, vol. 57, No. 2, Feb. 1954, pp. 149-152. (See Communication under 37 CFR § 1.98(a) (3)).
Taniyama et al., "Identification of Furan Derivatives and Aliphatic Dibasic Acids by Paper Chromatography", Toho Reiyon Kenkyu Hokoku, vol. 3, No. 1, 1956, pp. 23-29.
You et al., "Simultaneous H2 Generation and Biomass Upgrading in Water by an Efficient Noble-Metal-Free Bifunctional Electrocatalyst", Angew. Chem., vol. 128, 2016, pp. 10067-10071.

(56) References Cited

OTHER PUBLICATIONS

Zhang et al., "Controlled Deposition of Pt Nanoparticles on Fe3O4@Carbon Microspheres for Efficient Oxidation of 5-Hydroxymethylfurfural", RSC Advances, vol. 6, 2016, pp. 51229-51237.

Zhang et al., "Recent Advances in the Catalytic Synthesis of 2,5-Furandicarboxylic Acid and Its Derivatives", ACS Catal., vol. 5, 2015, pp. 6529-6544.

Zhao et al., "Oxidation of Primary Alcohols to Carboxylic Acids with Sodium Chlorite Catalyzed by TEMPO and Bleach", J. Org. Chem. vol. 64, No. 7, 1999, pp. 2564-2566.

* cited by examiner

300

320

OXIDATION CHEMISTRY ON FURAN ALDEHYDES

CROSS-REFERENCE TO RELATED APPLICATIONS

This application is a U.S. National Phase Patent Application under 35 U.S.C. § 371 of International Application No. PCT/US2016/052315, filed Sep. 16, 2016, which claims priority to and the benefit of U.S. Provisional Patent Application No. 62/220,181, filed Sep. 17, 2015, each of which is incorporated herein by reference in its entirety.

FIELD

The present disclosure relates generally to the production of halomethylfuroic and acyloxymethylfuroic compounds from furfural starting compounds, and more specifically to the production of 5-chloromethyl-2-furoic acid from 5-chloromethylfurfural, and 5-(octadecanoyloxy)methyl-2-furoic acid from 5-(octadecanoyloxy)methylfurfural.

BACKGROUND

Efforts to reduce dependence on fossil fuels as a feedstock for industrial chemicals have been undertaken for decades, with a particular focus on enabling economic feasibility of renewable feedstocks. Heightened efforts are being made to more effectively utilize renewable resources and develop "green" technologies, due to increased environmental concerns, continued issues of geopolitical stability, and renewed concerns for the ultimate depletion of fossil fuels.

For example, surfactants are a diverse group of compounds produced on an industrial scale with a diversity of applications including use in cleaning products (e.g. soaps, detergents), paints, adhesives, plastics, and pharmacological compositions. Surfactants are currently produced from petroleum-derived long chain alcohols by sulfonation.

Surfactants are often used for household cleaning, laundry and personal care, as well as in many industrial processes. Industrial uses include oil-field applications and oil spill clean-up. There is increasing interest in developing biomass-derived surfactants, including consumer demand for products from renewable resources.

Cellulose can be used to produce furan-based compounds by way of substituted (methyl)furfurals, such as 5-(halomethyl)furfural. What is desired in the art, however, are more direct methods of producing halomethylfuroic and acyloxymethylfuroic compounds, and other substituted fuoric compounds, from biomass and other renewable sources.

Thus, there remains a need in the art for new methods to produce substituted furoic compounds from renewable resources.

BRIEF SUMMARY

Provided herein are methods to produce substituted furan and tetrahydrofuran compounds from renewable resources. In one aspect, provided is a method of producing a halomethylfuroic acid, or a salt thereof, by: combining a halomethylfurfural and an oxidant to produce a halomethylfuroic acid, or a salt thereof, wherein the oxidant is: a compound of formula $W^b$-$O_2X^b$, wherein $W^b$ is a Group I cation and $X^b$ is halo; $W^d$-$O_3X^d$, wherein $W^d$ is a Group I cation and $X^d$ is halo; $HX^bO_2$, wherein $X^b$ is halo; $HX^dO_3$, wherein $X^d$ is halo; or $X^cO_2$, wherein $X^c$ is halo.

In some variations, the halomethylfurfural and oxidant are further combined with water. In one variation, the halomethylfurfural is 5-chloromethylfurfural and the halomethylfuroic acid is 5-chloromethyl-2-furoic acid. In certain variations, the halomethylfurfural and the oxidant are combined at a pH between 0 and 5.

In some aspects, provided herein are methods of producing compounds of formula (II):

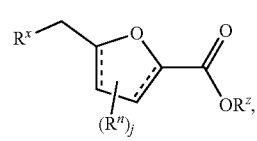

wherein:
  === is a double bond or a single bond;
  j is 2 when === is a double bond, or j is 6 when === is a single bond;
  each $R^n$ is independently H or alkyl;
  $R^x$ is halo, $OC(O)R^a$ or $OR^b$;
    wherein $R^a$ is H, aliphatic or aromatic, and $R^b$ is aliphatic; and
  $R^z$ is H or aliphatic.

In other aspects, provided herein are methods of producing compounds of formula (IIX):

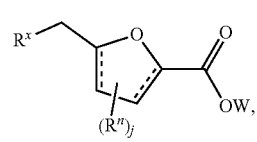

wherein:
  === is a double bond or a single bond;
  j is 2 when === is a double bond, or j is 6 when === is a single bond;
  each $R^n$ is independently H or alkyl;
  $R^x$ is halo, $OC(O)R^a$ or $OR^b$;
    wherein $R^a$ is H, aliphatic or aromatic, and $R^b$ is aliphatic; and
  W is a cation.

In some aspects, the compounds of formula (II) or formula (IIX) are produced by oxidizing a compound of formula (I):

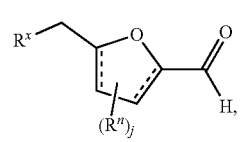

wherein:
  === is a double bond or a single bond;
  j is 2 when === is a double bond, or j is 6 when === is a single bond;
  each $R^n$ is independently H or alkyl; and
  $R^x$ is halo, $OC(O)R^a$ or $OR^b$;
    wherein $R^a$ is H, aliphatic or aromatic, and $R^b$ is aliphatic.

In one variation, the compound of formula (I) is 5-chloromethylfurfural and the compound of formula (II) is 5-chloromethyl-2-furoic acid. In certain variations, the compound of formula (I) and the oxidant are combined at a pH between 0 and 5.

In another variation, the compound of formula (I) is a compound of formula (I-Bi), the compound of formula (II) is a compound of formula (II-Bi), and the compound of formula (IIX) is a compound of formula (IIX-Bi), wherein:
the compound of formula (I-Bi) is:

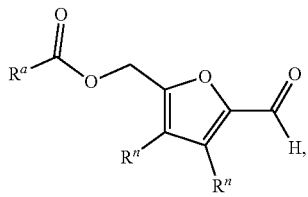

(I-Bi)

wherein each $R^n$ is independently H or alkyl; and
$R^a$ is H, aliphatic or aromatic;
the compound of formula (II-Bi) is:

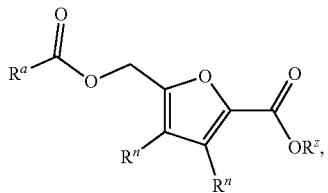

(II-Bi)

wherein $R^n$ and $R^a$ are as defined for formula (I-Bi); and
$R^z$ is H; and
the compound of formula (IIX-Bi) is:

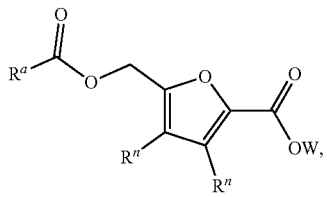

(IIX-Bi)

wherein W and $R^n$ and $R^a$ are as defined for formula (I-Bi); and
W is a cation.

In one variation, the compound of formula (I-Bi) is 5-(dodecanoyloxy)methylfurfural, and the compound of formula (II-Bi) is 5-((dodecanoyloxy)methyl)furan-2-carboxylic acid. In another variation, the compound of formula (IIX-Bi) is sodium 5-((dodecanoyloxy)methyl)furan-2-carboxylate.

In yet another aspect, provided herein is a method of producing a halomethylfuroic ester by combining a halomethylfurfural, an alcohol, and an oxidant to produce a halomethylfuroic ester, wherein the oxidant is a compound of formula $W^b$-$O_2X^b$, wherein $W^b$ is a Group I cation and $X^b$ is halo; $W^d$-$O_3X^d$, wherein $W^d$ is a Group I cation and $X^d$ is halo; $HX^bO_2$, wherein $X^b$ is halo; $HX^dO_3$, wherein $X^d$ is halo; or $X^cO_2$, wherein $X^c$ is halo. In certain variations, the halomethylfurfural and the oxidant are combined at a pH between 0 and 5.

In still another aspect, provided herein is a method of producing a compound of formula (II-Bi) by combining a compound of formula (I-Bi) with an alcohol and an oxidant to produce the compound of formula (II-Bi), wherein:
the compound of formula (I-Bi) is:

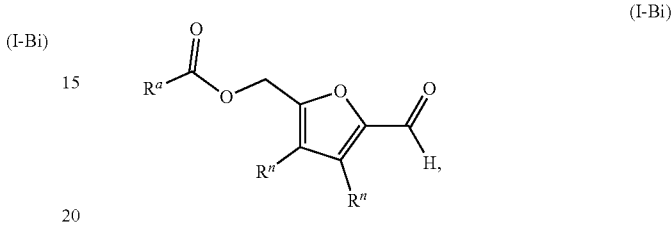

(I-Bi)

wherein each $R^n$ is independently H or alkyl; and
$R^a$ is H, aliphatic or aromatic;
the compound of formula (II-Bi) is:

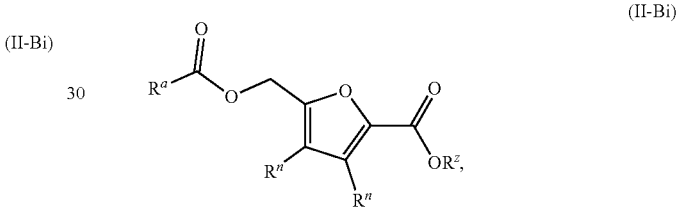

(II-Bi)

wherein $R^n$ and $R^a$ are as defined for formula (I-Bi); and
$R^z$ is aliphatic; and
the oxidant is a compound of formula $W^b$-$O_2X^b$, wherein $W^b$ is a Group I cation and $X^b$ is halo; $W^d$-$O_3X^d$, wherein $W^d$ is a Group I cation and $X^d$ is halo; $HX^bO_2$, wherein $X^b$ is halo; $HX^dO_3$, wherein $X^d$ is halo; or $X^cO_2$, wherein $X^c$ is halo.

DESCRIPTION OF THE FIGURES

The present application can be understood by reference to the following description taken in conjunction with the accompanying figures.

DETAILED DESCRIPTION

Figure 1A:
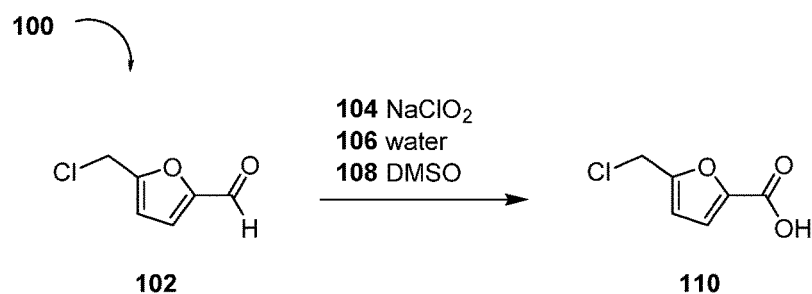
FIG. 1A depicts an exemplary reaction scheme of conversion of 5-chloromethylfurfural to 5-chloromethyl-2-furoic acid.

The following description sets forth exemplary methods, parameters and the like. It should be recognized, however, that such description is not intended as a limitation on the scope of the present disclosure but is instead provided as a description of exemplary embodiments.

In some aspects, provided herein are methods of producing compounds of formula (II):

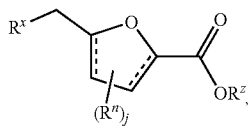

wherein:
  === is a double bond or a single bond;
  j is 2 when === is a double bond, or j is 6 when === is a single bond;
  each $R^n$ is independently H or alkyl;
  $R^x$ is halo, $OC(O)R^a$ or $OR^b$;
    wherein $R^a$ is H, aliphatic or aromatic, and $R^b$ is aliphatic; and
  $R^z$ is H or aliphatic.

In other aspects, provided herein are methods of producing compounds of formula (IIX):

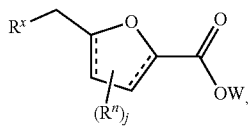

wherein:
  === is a double bond or a single bond;
  j is 2 when === is a double bond, or j is 6 when === is a single bond;
  each $R^n$ is independently H or alkyl;
  $R^x$ is halo, $OC(O)R^a$ or $OR^b$;
    wherein $R^a$ is H, aliphatic or aromatic, and $R^b$ is aliphatic; and
  W is a cation.

In some variations, the compounds of formula (II) are compounds of formula (II-i):

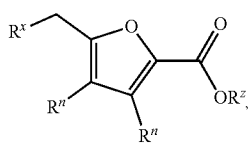

wherein:
  each $R^n$ is independently H or alkyl;
  $R^x$ is halo, $OC(O)R^a$ or $OR^b$,
    wherein $R^a$ is H, aliphatic or aromatic, and $R^b$ is aliphatic; and
  $R^z$ is H or aliphatic.

In other variations, the compounds of formula (IIX) are compounds of formula (IIX-i):

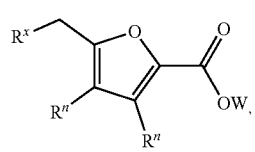

wherein:
  each $R^n$ is independently H or alkyl;
  $R^x$ is halo, $OC(O)R^a$ or $OR^b$,
    wherein $R^a$ is H, aliphatic or aromatic, and $R^b$ is aliphatic; and
  W is a cation.

In yet other variations, the compounds of formula (II) are compounds of formula (II-ii):

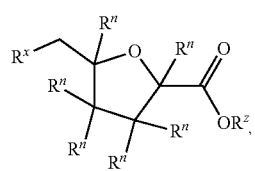

wherein:
  each $R^n$ is independently H or alkyl;
  $R^x$ is halo, $OC(O)R^a$ or $OR^b$,
    wherein $R^a$ is H, aliphatic or aromatic, and $R^b$ is aliphatic; and
  $R^z$ is H or aliphatic.

In still other variations, the compounds of formula (IIX) are compounds of formula (IIX-ii):

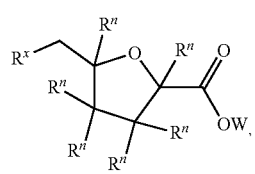

wherein:
  each $R^n$ is independently H or alkyl;
  $R^x$ is halo, $OC(O)R^a$ or $OR^b$,
    wherein $R^a$ is H, aliphatic or aromatic, and $R^b$ is aliphatic; and
  W is a cation.

Such compounds of formula (II) or formula (IIX) may be produced by oxidizing compounds of formula (I):

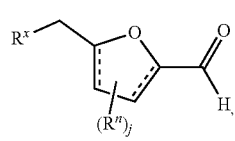

wherein:
  === is a double bond or a single bond;
  j is 2 when === is a double bond, or j is 6 when === is a single bond;
  each $R^n$ is independently H or alkyl; and
  $R^x$ is halo, $OC(O)R^a$ or $OR^b$;
    wherein $R^a$ is H, aliphatic or aromatic, and $R^b$ is aliphatic.

In some variations, the compounds of formula (I) are compounds of formula (I-i):

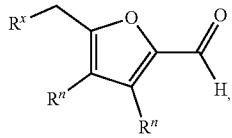
(I-i)

wherein:
  each $R^n$ is independently H or alkyl; and
  $R^x$ is halo, $OC(O)R^a$ or $OR^b$;
    wherein $R^a$ is H, aliphatic or aromatic, and $R^b$ is aliphatic.

In other variations, the compounds of formula (I) are compounds of formula (I-ii):

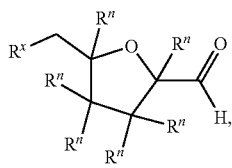
(I-ii)

wherein:
  each $R^n$ is independently H or alkyl; and
  $R^x$ is halo, $OC(O)R^a$ or $OR^b$;
    wherein $R^a$ is H, aliphatic or aromatic, and $R^b$ is aliphatic.

The compounds of formula (I) used in the methods described herein may be obtained from any commercially available sources or produced according to any suitable methods known in the art.

The compounds of formula (I), including compounds of formulae (I-i) and (I-ii), may be converted to compounds of formula (II) or formula (IIX), including compounds of formula (II-i), (II-ii), (IIX-i), and (IIX-ii), in the presence of:
  (i) water or alcohol, and
  (ii) an oxidant selected from halite compounds, halate compounds, halous acid compounds, halic acid compounds, or halogen dioxide compounds, or any combinations thereof.

In some variations, the compound of formula (I) is a compound of formula (I-Ai):

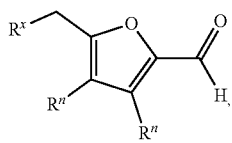
(I-Ai)

wherein:
  $R^n$ is as defined above for formula (I); and
  X is halo.

Figure 1B:
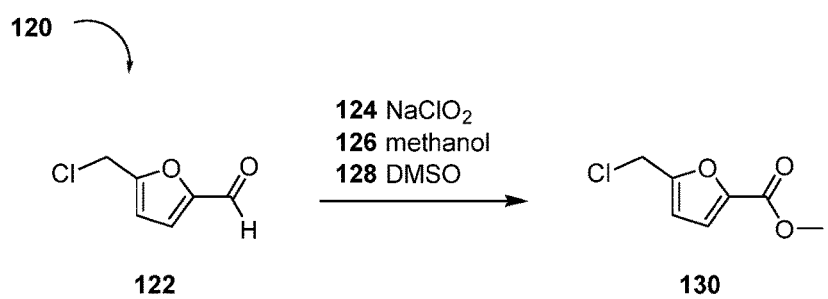
FIG. 1B depicts an exemplary reaction scheme of conversion of 5-chloromethylfurfural to methyl 5-(chloromethyl)furan-2-carboxylate.

For example, FIGS. 1A and 1B depict exemplary reactions involving the oxidation of a compound of formula (I-Ai) with water and alcohol, respectively.

In other variations, the compound of formula (I) is a compound of formula (I-Bi):

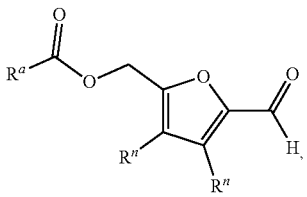
(I-Bi)

wherein:
  $R^n$ is as defined above for formula (I); and
  $R^a$ is H, aliphatic or aromatic.

Figure 2A:
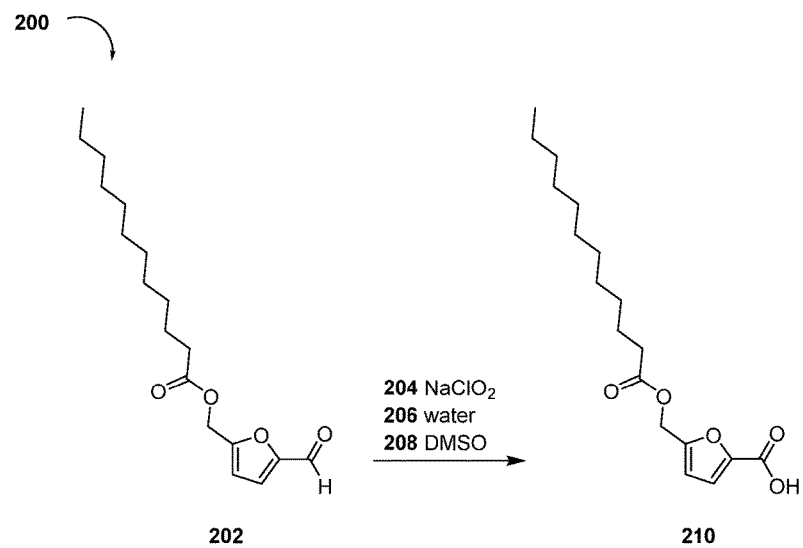
FIG. 2A depicts an exemplary reaction scheme of the conversion of 5-(dodecanoyloxy)methylfurfural to 5-((dodecanoyloxy)methyl)furan-2-carboxylic acid.
Figure 2B:
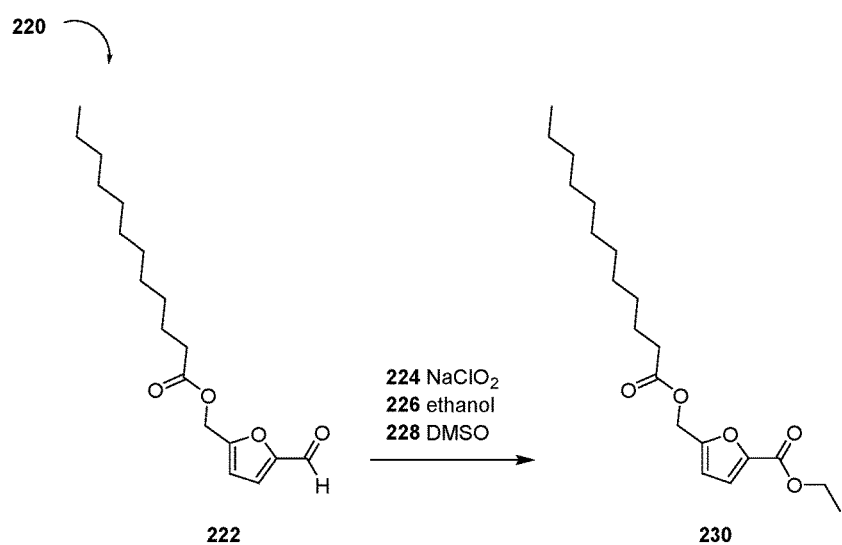
FIG. 2B depicts an exemplary reaction scheme of the conversion of 5-(dodecanoyloxy)methylfurfural to ethyl 5-((dodecanoyloxy)methyl)furan-2-carboxylate.

For example FIGS. 2A and 2B depict exemplary reactions involving the oxidation of a compound of formula (I-Bi) with water and alcohol, respectively.

In other variations, the compound of formula (I) is a compound of formula (I-Ci):

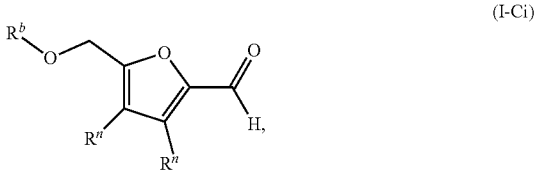
(I-Ci)

wherein:
  $R^n$ is as defined above for formula (I); and
  $R^b$ is aliphatic.

Figure 3A:
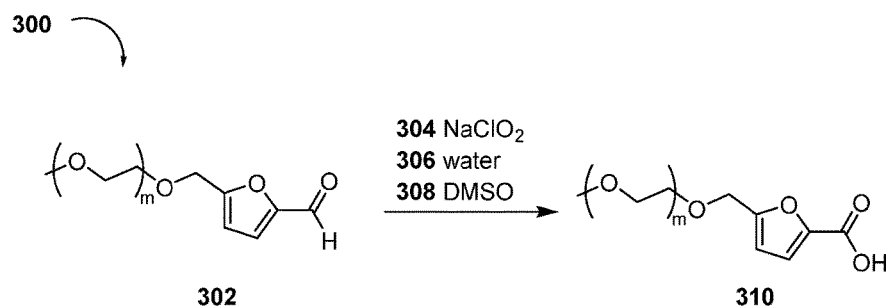
FIG. 3A depicts an exemplary reaction scheme of the oxidation of an ether of 5-hydroxymethylfurfural.
Figure 3B:
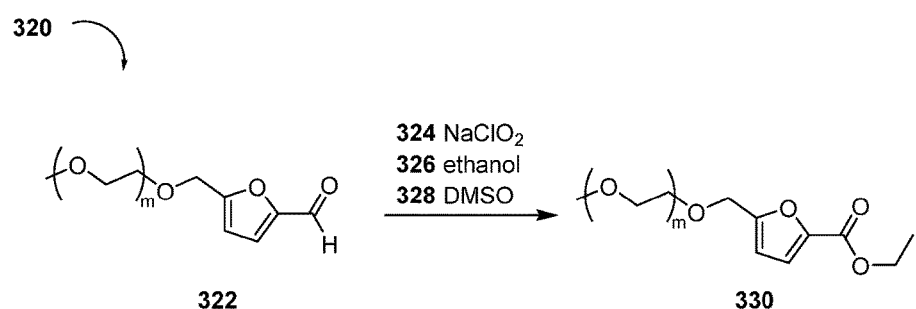
FIG. 3B depicts an exemplary reaction scheme of the conversion of an ether of 5-hydroxymethylfurfural to an ether of ethyl 5-hydroxymethylfuran-2-carboxylate.

For example FIGS. 3A and 3B depict exemplary reactions involving the oxidation of a compound of formula (I-Ci) with water and alcohol, respectively.

In other variations, the compound of formula (I) is a compound of formula (I-Bii):

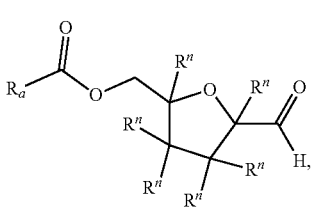
(I-Bii)

wherein:
  $R^n$ is as defined above for formula (I); and
  $R^a$ is H, aliphatic or aromatic.

When the compound of formula (I), including a compound of formulae (I-Ai), (I-Bi), or (I-Ci), is oxidized in the presence of water, a compound of formula (II), including a compound of formulae (II-Ai), (II-Bi) or (II-Ci), or a salt thereof is produced.

In some variations, the salt of the compound of formula (II) is a compound of formula (IIX-i):

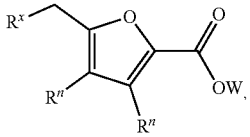
(IIX-i)

wherein:
   each $R''$ is independently H or alkyl;
   $R^x$ is halo, $OC(O)R^a$ or $OR^b$;
      wherein $R^a$ is H, aliphatic or aromatic, and $R^b$ is aliphatic; and
   W is a cation.

In other variations, the salt of the compound of formula (II) is a compound of formula (IIX-ii):

(IIX-ii)

wherein:
   each $R''$ is independently H or alkyl;
   $R^x$ is halo, $OC(O)R^a$ or $OR^b$;
      wherein $R^a$ is H, aliphatic or aromatic, and $R^b$ is aliphatic; and
   W is a cation.

In some variations, W is a monoatomic cation, while in other variations, W is a polyatomic cation. In some embodiments, W is a Group I or Group II cation. It should be understood that the cation W may vary depending on the oxidant used. For example, in certain embodiments, when $NaClO_2$ is used as the oxidant, W is $Na^+$.

The compounds of formulae (I) and (II), and the oxidants used in the methods described herein are further provided below.

Compounds of Formula (I)

The compounds of formula (I) that may be oxidized according to the methods described herein include:

(I)

wherein:
   === is a double bond or a single bond;
   j is 2 when === is a double bond, or j is 6 when === is a single bond;
   each $R''$ is independently H or alkyl; and
   $R^x$ is halo, $OC(O)R^a$ or $OR^b$;
      wherein $R^a$ is H, aliphatic or aromatic, and $R^b$ is aliphatic.

In some embodiments, === is a double bond and j is 2. In other embodiments, === is a single bond and j is 6.

Compounds of Formula (I-i)

In some variations, === is a double bond, j is 2, and the compound of formula (I) is a compound of formula (I-i):

(I-i)

wherein:
   each $R''$ is independently H or alkyl; and
   $R^x$ is halo, $OC(O)R^a$ or $OR^b$;
      wherein $R^a$ is H, aliphatic or aromatic, and $R^b$ is aliphatic.

In some variations, both $R''$ are H. In certain variations, one $R''$ is alkyl and the other $R''$ is H. In yet other variations, both $R''$ are alkyl.

As used herein, "alkyl" refers to a linear or branched saturated hydrocarbon chain. Examples of alkyl groups include methyl, ethyl, n-propyl, iso-propyl, n-butyl, sec-butyl, tert-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl. In some embodiments, alkyl as used in compounds of formula (I) and other compounds described herein (as applicable) and the corresponding alcohol used in the methods described herein has 1 to 40 carbon atoms (i.e., $C_{1-40}$), 1 to 30 carbon atoms (i.e., $C_{1-30}$ alkyl), 1 to 20 carbon atoms (i.e., $C_{1-20}$ alkyl), 1 to 15 carbon atoms (i.e., $C_{1-15}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), or 1 carbon atom (i.e., $C_1$ alkyl).

In some variations, $R^x$ is halo, and the compound of formula (I-i) is a compound of formula (I-Ai):

(I-Ai)

wherein:
   each $R''$ is independently H or alkyl; and
   X is halo.

For example, in one embodiment, X is chloro, while in another embodiment X is bromo.

In one embodiment, each $R''$ is H, X is chloro, and the compound of formula (I-Ai) is 5-chloromethylfurfural. Thus, in one embodiment, the compound of formula (I-Ai) is:

In another embodiment, each $R''$ is H, X is bromo, and the compound of formula (I-Ai) is 5-bromomethylfurfural. Thus, in one embodiment, the compound of formula (I-Ai) is:

In other variations, $R^x$ is $OC(O)R^a$, and the compound of formula (I-i) is a compound of formula (I-Bi):

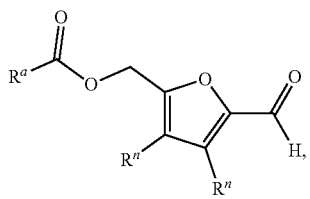

(I-Bi)

wherein:
each $R^n$ is independently H or alkyl; and
$R^a$ is H, aliphatic or aromatic.

In some embodiments of the compound of formula (I-Bi), $R^a$ is an aliphatic group. Aliphatic groups include acyclic or cyclic, saturated or unsaturated carbon groups, excluding aromatic groups. Aside from hydrogen, other elements may be bound to, or incorporated into portions of, the carbon chain, including, for example, oxygen, nitrogen and sulfur.

Examples of aliphatic groups include methyl, ethyl, propyl, iso-propyl, n-butyl, sec-butyl, tert-butyl, pentyl, 2-pentyl, iso-pentyl, neo-pentyl, hexyl, 2-hexyl, 3-hexyl, 3-methylpentyl, ethenyl, ethynyl, propenyl, propynyl, 1,2-butandienyl, 1-butynyl, butenyl, cyclohexyl, cyclohexenyl, and pentanyl. When an aliphatic residue having a specific number of carbons is named, all geometric isomers having that number of carbons may be encompassed. Further, it should be understood that when a range of values is listed, it is intended to encompass each value and sub-range within the range. For example, "$C_{1-6}$ aliphatic" (which may also be referred to as 1-6C aliphatic, C1-C6 aliphatic, or C1-6 aliphatic) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ aliphatic.

The aliphatic group may be saturated or unsaturated (e.g., monounsaturated or polyunsaturated). In some variations, $R^a$ is a saturated aliphatic group. Suitable examples of saturated aliphatic groups include alkyl groups, such as methyl, ethyl, propyl and butyl. In other variations, $R^a$ is an unsaturated aliphatic group. In certain variations, $R^a$ is $C_1$-$C_{18}$ aliphatic. For example, in some variations, $R^a$ is saturated $C_{11}$, saturated $C_{13}$, saturated $C_{15}$, saturated $C_{17}$, saturated $C_{19}$, monounsaturated $C_{17}$, or polyunsaturated $C_{17}$ aliphatic.

In some variations, the aliphatic group may be selected from alkyl, cycloalkyl, ether, ester, carboxylic acid, alkene, and alkyne. In some variations, the aliphatic group is further substituted with one or more substituents independently selected from hydroxyl amide, acid, cyano, alkoxy, ester, ether, or nitro.

In certain variations, $R^a$ is $C_1$-$C_{40}$ alkyl, $C_1$-$C_{30}$ alkyl, $C_5$-$C_{30}$ alkyl, $C_{10}$-$C_{30}$ alkyl, or $C_{15}$-$C_{25}$ alkyl. In some embodiments, $R^a$ is linear. In other embodiments, $R^a$ is branched. In one embodiment, $R^a$ is linear $C_{17}$ alkyl. In another embodiment, $R^a$ is linear $C_{11}$ alkyl.

In one variation, each $R^n$ is H, $R^a$ is an aliphatic group, wherein the aliphatic group is linear $C_{17}$ alkyl, and the compound of formula (I-Bi) is 5-(octadecanoyloxy)methyl-furfural (or (5-formylfuran-2-yl)methyl octadecanoate). Thus, in one variation, the compound of formula (I-Bi) is:

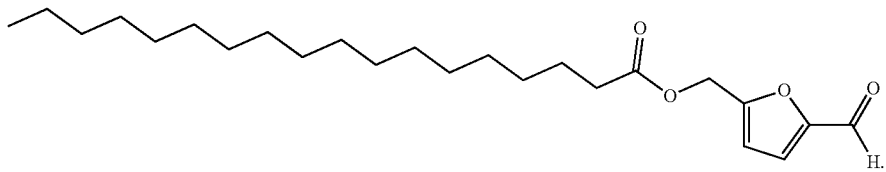

In another variation, each $R^n$ is H, $R^a$ is an aliphatic group, wherein the aliphatic group is linear $C_{11}$ alkyl, and the compound of formula (I-Bi) is 5-(dodecanoyloxy)methyl-furfural (or (5-formylfuran-2-yl)methyl dodecanoate). Thus, in one variation, the compound of formula (I-Bi) is:

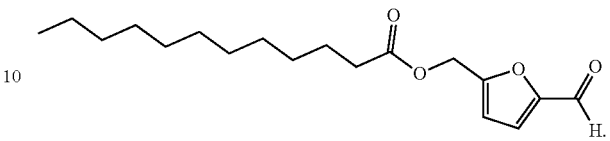

In other embodiments of the compound of formula (I-Bi), $R^a$ is an aromatic group. Aromatic groups may include aryl and heteroaryl groups, "Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments, aryl as used herein has 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein has 3 to 20 ring carbon atoms (i.e., $C_{3-20}$ heteroaryl), 3 to 12 ring carbon atoms (i.e., $C_{3-12}$heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl does not encompass or overlap with aryl as defined above.

In some variations, the heteroaryl is pyridyl. In certain variations, $R^a$ is pyridin-2yl, pyridin-3yl, or pyridin-4yl. For example, in one variation, each $R^n$ is H, $R^a$ is pyridin-4yl, and the compound of formula (I-Bi) is (5-formylfuran-2-yl) methyl isonicotinate. Thus, in one variation, the compound of formula (I-Bi) is:

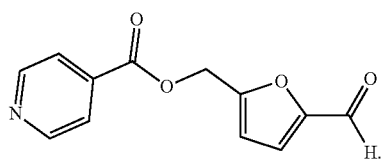

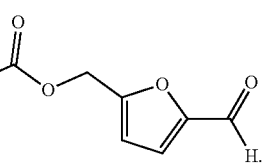

For example, in one variation each R" is H, Rᵃ is pyridin-2yl, and the compound of formula (I-Bi) is (5-formylfuran-2-yl)methyl picolinate. Thus, in one variation, the compound of formula (I-Bi) is:

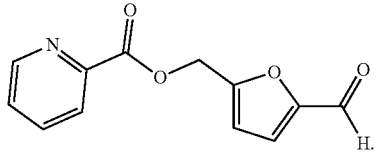

In other variations, Rᵃ is H. For example, in one variation, each R" is H, Rᵃ is H, and the compound of formula (I-Bi) is (5-formylfuran-2-yl)methyl formate. Thus, in one variation, the compound of formula (I-Bi) is:

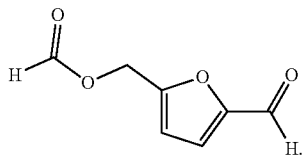

In other variations of formula (I-i), Rˣ is ORᵇ, and the compound of formula (I-i) is a compound of formula (I-Ci):

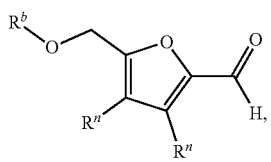

(I-Ci)

wherein:
    each R" is independently H or alkyl; and
    Rᵇ is aliphatic.
For example, in one embodiment, Rᵇ is a linear alkyl, while in another embodiment, Rᵇ is an ether.
In one variation, each R" is H, Rᵇ is a polyethylene glycol methyl ether, and the compound of formula (I-Ci) is:

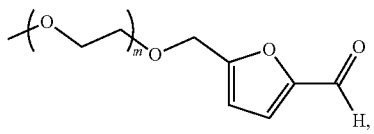

wherein m is an integer greater than 1.
For example, in one variation, m is 5, and the compound of formula (I-Ci) is:

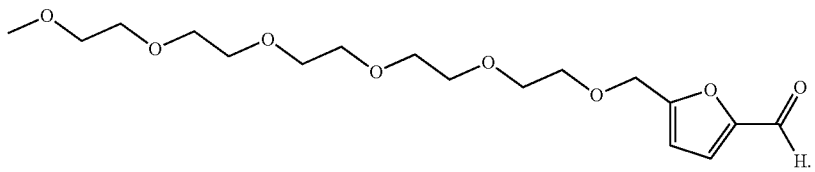

Compounds of Formula (I-ii)
In some embodiments, ═ is a double bond, j is 6, and the compound of formula (I) is a compound of formula (I-ii):

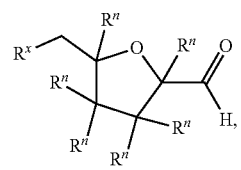

(I-ii)

wherein:
    each R" is independently H or alkyl; and
    Rˣ is halo, OC(O)Rᵃ or ORᵇ;
        wherein Rᵃ is H, aliphatic or aromatic, and Rᵇ is aliphatic.

In some variations, each R" is H. In certain variations, one R" is alkyl and each of the remaining R" is H. In other variations, two R" are independently alkyl, and each of the remaining R" is H. In other variations, three R" are independently alkyl, and each of the remaining R" is H. In still other variations, four R" are independently alkyl, and each of the remaining R" is H. In yet other variations, five R" are independently alkyl, and the remaining R" is H. In other variations, each R" is independently alkyl.

In some variations, Rˣ is halo, and the compound of formula (I-ii) is a compound of formula (I-Aii):

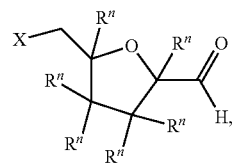

(I-Aii)

wherein:
    each R" is independently H or alkyl; and
    X is halo.
For example, in one embodiment, X is chloro, while in another embodiment X is bromo.
In one embodiment, each R" is H, X is chloro, and the compound of formula (I-Aii) is 5-(chloromethyl)tetrahydrofuran-2-carbaldehyde. Thus, in one embodiment, the compound of formula (I-Aii) is:

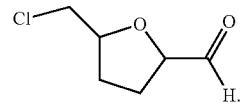

In another embodiment, each R" is H, X is bromo, and the compound of formula (I-Aii) is 5-(bromomethyl)tetrahydrofuran-2-carbaldehyde. Thus, in one embodiment, the compound of formula (I-Aii) is:

[Structure: Br-CH2-tetrahydrofuran-CHO]

In other variations, $R^x$ is OC(O)$R^a$, and the compound of formula (I-ii) is a compound of formula (I-Bii):

[Structure (I-Bii)]

wherein:
 each R" is independently H or alkyl; and
 $R^a$ is H, aliphatic or aromatic.

In some embodiments of the compound of formula (I-Bii), $R^a$ is aliphatic.

In one variation, each R" is H, $R^a$ is an aliphatic group, wherein the aliphatic group is linear $C_{11}$ alkyl, and the compound of formula (I-Bii) is (5-formyltetrahydrofuran-2-yl)methyl dodecanoate (or (5-formyltetrahydrofuran-2-yl) methyl dodecanoate). Thus, in one variation, the compound of formula (I-Bii) is:

[Structure: dodecanoate ester of (5-formyltetrahydrofuran-2-yl)methanol]

In other variations, $R^a$ is aromatic. In some variations, $R^a$ is a heteroaryl, wherein the heteroaryl is pyridyl. In certain variations, $R^a$ is pyridin-2yl, pyridin-3yl, or pyridin-4yl. For example, in one variation, each R" is H, $R^a$ is pyridin-4yl, and the compound of formula (I-Bii) is (5-formyltetrahydrofuran-2-yl)methyl isonicotinate. Thus, in one variation, the compound of formula (I-Bii) is:

[Structure: isonicotinate ester of (5-formyltetrahydrofuran-2-yl)methanol]

In other variations of formula (I-ii), $R^x$ is $OR^b$, and the compound of formula (I-ii) is a compound of formula (I-Cii):

[Structure (I-Cii)]

wherein:
 each R" is independently H or alkyl; and
 $R^b$ is aliphatic.

For example, in one embodiment, $R^b$ is a linear alkyl, while in another embodiment, $R^b$ is ether.

In one variation, each R" is H, $R^b$ is a polyethylene glycol methyl ether, and the compound of formula (I-Cii) is:

[Structure: PEG ether of (5-formyltetrahydrofuran-2-yl)methanol]

wherein m is an integer greater than 1.

Compounds of Formula (II)

The compounds of formula (I) can be oxidized according to the methods described herein to produce compounds of formula (II):

[Structure (II)]

wherein:
 === is a double bond or a single bond;
 j is 2 when === is a double bond, or j is 6 when === is a single bond;
 each R" is independently H or alkyl;
 $R^x$ is halo, OC(O)$R^a$ or $OR^b$;
  wherein $R^a$ is H, aliphatic or aromatic, and $R^b$ is aliphatic; and
 $R^z$ is H or aliphatic.

In some embodiments, === is a double bond and j is 2. In other embodiments, === is a single bond and j is 6.

Compounds of Formula (II-i)

In some variations, === is a double bond, j is 2, and the compound of formula (II) is a compound of formula (II-i):

[Structure (II-i)]

wherein:
 each R" is independently H or alkyl;
 $R^x$ is halo, OC(O)$R^a$ or $OR^b$;
  wherein $R^a$ is H, aliphatic or aromatic, and $R^b$ is aliphatic; and
 $R^z$ is H or aliphatic.

In some variations, both R″ are H. In certain variations, one R″ is alkyl and the other R″ is H. In yet other variations, both R″ are alkyl.

In some variations, $R^z$ is H, and the compound of formula (II-i) is a furoic acid. In other variations, $R^z$ is aliphatic, and the compound of formula (II-i) is an aliphatic furoic ester (or aliphatic furoate). In still other variations, $R^z$ is alkyl, and the compound of formula (II-i) is an alkyl furoic ester (or alkyl furoate). For example, in certain embodiments, $R^z$ is $C_1$-$C_{20}$ alkyl, $C_1$-$C_{15}$ alkyl, $C_1$-$C_{10}$ alkyl, $C_5$-$C_{10}$ alkyl, or $C_1$-$O_5$ alkyl. In some embodiments, $R^z$ is methyl, ethyl, iso-propyl, or butyl. It should be generally understood that when the furfural starting compound of formula (I-i) is combined with water and an oxidant, a compound of formula (II-i) may be produced wherein $R^z$ is H. When the furfural starting compound of formula (I-i) is combined with an alcohol and an oxidant, a compound of formula (II-i) may be produced wherein $R^z$ is alkyl. In some variations, when the furfural starting compound of formula (I-i) is combined with an alcohol and an oxidant, a compound of formula (II-i) may be produced wherein $R^z$ is aliphatic.

For example, with reference to FIG. 1A, process 100 depicts an exemplary process to produce compound 110, one example of a compound of formula (II-i) wherein $R^z$ is H. Compound 102 (one example of a compound of formula (I-i)) is combined with oxidant compound 104, water 106, and dimethyl sulfoxide 108 to produce compound 110. Any suitable oxidant compounds described herein may be used in process 100. In some variations of process 100, compound 104 is produced in situ.

With reference to FIG. 1B, process 120 depicts an exemplary process to produce compound 130, one example of a compound of formula (II-i) wherein $R^z$ is alkyl. Compound 122 (one example of a compound of formula (I-i)) is combined with oxidant compound 124, alcohol 126, and dimethyl sulfoxide 128 to produce compound 130. Any suitable oxidant compounds described herein may be used in process 120. In some variations of process 120, compound 124 is produced in situ.

It should generally be understood that in converting a compound of formula (I-i) to a compound of formula (II-i), the R″ and $R^x$ of the compound of formula (I-i) are the same R″ and $R^x$ of the compound of formula (II-i).

Compounds 102 and 122 are both compounds of formula (I-i) wherein $R^x$ is halo, and therefore are also examples of compounds of formula (I-Ai). Compounds 110 and 130 are both compounds of formula (II-i) wherein $R^x$ is halo, and therefore are also examples of compounds of formula (II-Ai). It should be understood that while processes 100 and 120 depict exemplary processes to produce compounds of formula (II-Ai) from compounds of formula (I-Ai), in some variations, compounds of formula (I-Bi) (compounds of formula (I-i) wherein $R^x$ is OC(O)$R^a$, wherein $R^a$ is H, aliphatic or aromatic) may be used to produce compounds of formula (II-Bi) (compounds of formula (II-i) wherein $R^x$ is OC(O)$R^a$, wherein $R^a$ is H, aliphatic or aromatic).

Compounds of Formula (II-Ai)

In some variations, $R^x$ is halo, and the compound of formula (II-i) is a compound of formula (II-Ai), or a salt thereof:

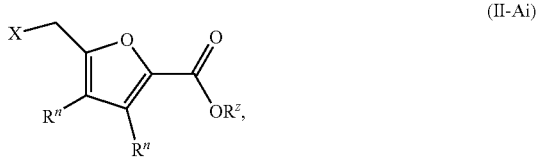

(II-Ai)

wherein:
each R″ is independently H or alkyl;
$R^z$ is H or aliphatic; and
X is halo.

For example, in one embodiment, X is chloro, while in another embodiment X is bromo.

In one embodiment, each R″ is H, $R^z$ is H, X is chloro, and the compound of formula (II-Ai) is 5-chloromethyl-2-furoic acid. Thus, in one embodiment, the compound of formula (II-Ai) is:

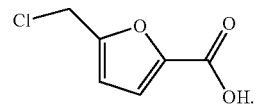

In another embodiment, each R″ is H, $R^z$ is H, X is bromo, and the compound of formula (II-Ai) is 5-bromomethyl-2-furoic acid. Thus, in one embodiment, the compound of formula (II-Ai) is:

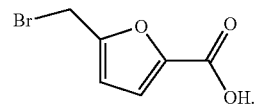

For example, with reference again to FIG. 1A, process 100 depicts an exemplary process to produce compound 110, 5-chloromethyl-2-furoic acid (one example of a compound of formula (II-Ai) wherein each R″ is H, $R^z$ is H, and X is chloro). Compound 102, 5-chloromethylfurfural (one example of a compound of formula (I-Ai) wherein each $R^a$ is H and X is chloro), is combined with oxidant compound 104, water 106, and dimethyl sulfoxide 108 to produce compound 110.

Compounds of Formula (II-Bi)

In other variations, $R^x$ is OC(O)$R^a$, and the compound of formula (II-i) is a compound of formula (II-Bi), or a salt thereof:

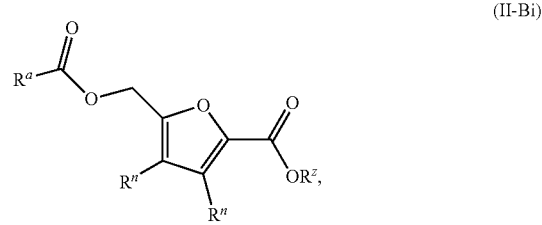

(II-Bi)

wherein:
each R″ is independently H or alkyl;
$R^z$ is H or aliphatic; and
$R^a$ is H, aliphatic or aromatic.

In some variations, $R^a$ is $C_1$-$C_{40}$ alkyl, $C_1$-$C_{30}$ alkyl, $C_5$-$C_{30}$ alkyl, $C_{10}$-$C_{30}$ alkyl, or $C_{15}$-$C_{25}$ alkyl. In one embodiment, $R^x$ is OC(O)$R^a$, wherein $R^a$ is $C_{17}$ alkyl.

In one variation, each R″ is H, $R^z$ is H, $R^a$ is linear $C_{17}$ alkyl, and the compound of formula (II-Bi) is 5-(octadecanoyloxy)methyl-2-furoic acid (or 5-((octadecanoyloxy)methyl)furan-2-carboxylic acid). Thus, in one embodiment, the compound of formula (II-Bi) is:

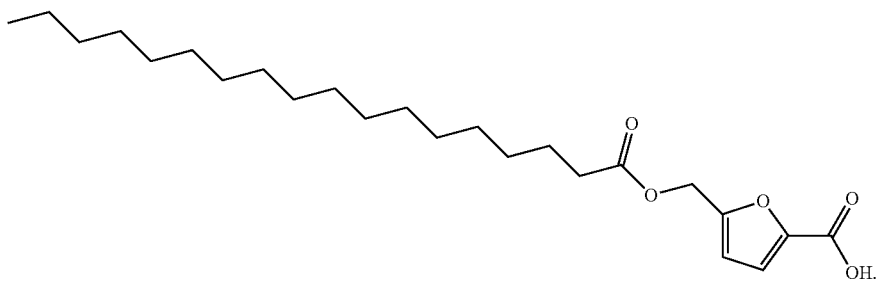 [SMILES: CCCCCCCCCCCCCCCCCC(=O)OCc1ccc(C(=O)O)o1]

In another variation, each $R^n$ is H, $R^z$ is H, $R^a$ is linear $C_{11}$ alkyl, and the compound of formula (II-Bi) is 5-(dodecanoyloxy)methyl-2-furoic acid (or 5-((dodecanoyloxy)methyl)furan-2-carboxylic acid). Thus, in one embodiment, the compound of formula (II-Bi) is:

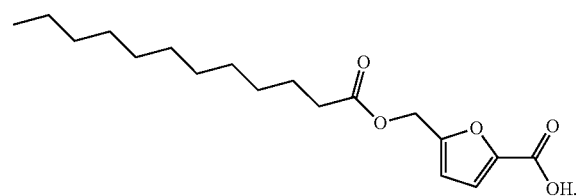 [SMILES: CCCCCCCCCCCC(=O)OCc1ccc(C(=O)O)o1]

For example, with reference to FIG. 2A, process 200 depicts an exemplary process to produce compound 210, 5-(dodecanoyloxy)methyl-2-furoic acid (one example of a compound of formula (II-Bi) wherein each $R^n$ is H, $R^a$ is linear $C_{11}$ alkyl, and $R^z$ is H). Compound 202, 5-(dodecanoyloxy)methylfurfural (one example of a compound of formula (I-i) wherein each $R^n$ is H and $R^a$ is linear $C_{11}$ alkyl) is combined with oxidant compound 204, water 206, and dimethyl sulfoxide 208 to produce compound 210. Any suitable oxidant compounds described herein may be used in process 200. In some variations of process 200, oxidant compound 204 is $LiClO_2$. In other variations, oxidant compound 204 is $KClO_3$. It should be understood that in some variations, process 200 may include additional steps. Additional steps may include, for example, isolating compound 210 through solvent extraction, precipitation, filtration, or chromatography.

In another variation, each $R^n$ is H, $R^z$ is H, $R^a$ is pyridin-4yl, and the compound of formula (I-Bi) is 5-((isonicotinoyloxy)methyl)furan-2-carboxylic acid. Thus, in one variation, the compound of formula (II-Bi) is:

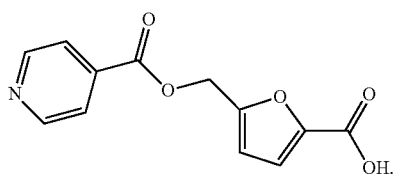 [SMILES: O=C(OCc1ccc(C(=O)O)o1)c1ccncc1]

In yet another variation, $R^n$ and $R^z$ are H, $R^a$ is H, and the compound of formula (II-Bi) is 5-((formyloxy)methyl)furan-2-carboxylic acid. Thus, in one variation, the compound of formula (II-Bi) is:

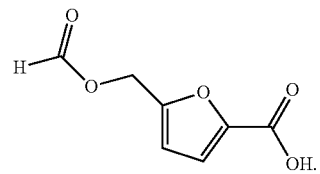 [SMILES: O=COCc1ccc(C(=O)O)o1]

Compounds of Formula (II-Ci)

In other variations of formula (II-i), $R^x$ is $OR^b$, and the compound of formula (II-i) is a compound of formula (II-Ci):

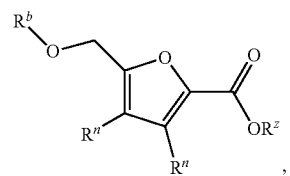

(II-Ci)

wherein:
each $R^n$ is independently H or alkyl;
$R^z$ is H or aliphatic; and
$R^b$ is aliphatic.

For example, in one embodiment, $R^b$ is a linear alkyl, while in another embodiment, $R^b$ is an ether.

In one variation, each $R^n$ is H, $R^z$ is H, $R^b$ is a polyethylene glycol methyl ether, and the compound of formula (II-Ci) is:

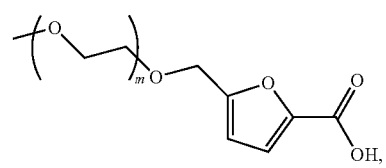

wherein m is an integer greater than 1.

In some embodiments $R^z$ is H. For example, with reference to FIG. 3A, process 300 depicts an exemplary process to produce compound 310, one example of a compound of formula II-Ci wherein each $R^n$ is H, $R^z$ is H, and $R^b$ is a polyethylene glycol methyl ether. Compound 302, one example of a compound of formula (I-Ci) wherein each $R^n$ is H and $R^b$ is a polyethenylene glycol methyl ether, is combined with oxidant compound 304, water 306, and dimethyl sulfoxide 308 to produce compound 310.

In other embodiments, $R^z$ is aliphatic. With reference to FIG. 3B, process 320 depicts an exemplary process to produce compound 330, one example of a compound of formula (II-Ci) wherein $R^z$ is alkyl. Compound 322 is combined with oxidant compound 324, alcohol 326, and dimethyl sulfoxide 328 to produce compound 330, wherein alcohol 326 is ethanol and $R^z$ is ethyl.

In one variation, m is 5, and the compound of formula (II-Ci) is:

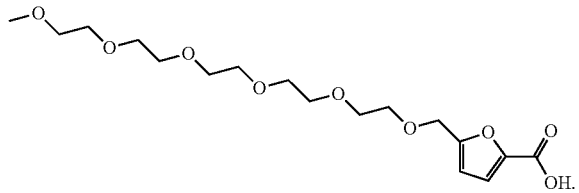 [SMILES: COCCOCCOCCOCCOCCOCc1ccc(C(=O)O)o1]

Compounds of Formula (II-ii)

In some embodiments, ═══ is a double bond, j is 6, and the compound of formula (II) is a compound of formula (II-ii):

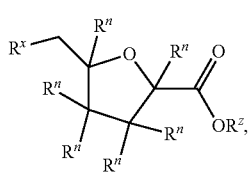

(II-ii)

wherein:
  each $R''$ is independently H or alkyl;
  $R^z$ is H or aliphatic; and
  $R^x$ is halo, OC(O)$R^a$ or O$R^b$;
    wherein $R^a$ is H, aliphatic or aromatic, and $R^b$ is aliphatic.

In some variations, each $R''$ is H. In certain variations, one $R''$ is alkyl and each of the remaining $R''$ is H. In other variations, two $R''$ are independently alkyl, and each of the remaining $R''$ is H. In other variations, three $R''$ are independently alkyl, and each of the remaining $R''$ is H. In still other variations, four $R''$ are independently alkyl, and each of the remaining $R''$ is H. In yet other variations, five $R''$ are independently alkyl, and the remaining $R''$ is H. In other variations, each $R''$ is independently alkyl.

In some variations, $R^z$ is H, and the compound of formula (II-ii) is a tetrahydrofuroic acid. In other variations, $R^z$ is aliphatic, and the compound of formula (II-ii) is an aliphatic tetrahydrofuroic ester (or aliphatic tetrahydrofuroate). In still other variations, $R^z$ is alkyl, and the compound of formula (II-ii) is an alkyl tetrahydrofuroic ester (or alkyl tetrahydrofuroate). For example, in certain embodiments, $R^z$ is $C_1$-$C_{20}$ alkyl, $C_1$-$C_{15}$ alkyl, $C_1$-$C_{10}$ alkyl, $C_5$-$C_{10}$ alkyl, or $C_1$-$C_5$ alkyl. In some embodiments, $R^z$ is methyl, ethyl, iso-propyl, or butyl. It should be generally understood that when the furfural starting compound of formula (I-ii) is combined with water and an oxidant, a compound of formula (II-ii) may be produced wherein $R^z$ is H. When the furfural starting compound of formula (I-ii) is combined with an alcohol and an oxidant, a compound of formula (II-ii) may be produced wherein $R^z$ is alkyl. In some embodiments, when the furfural starting compound of formula (I-ii) is combined with an alcohol and an oxidant, a compound of formula (II-ii) may be produces wherein $R^z$ is aliphatic.

In some variations, $R^x$ is halo, and the compound of formula (II-ii) is a compound of formula (II-Aii):

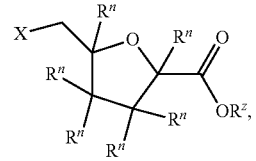

(II-Aii)

wherein:
  each $R''$ is independently H or alkyl;
  $R^z$ is H or aliphatic; and
  X is halo.

For example, in one embodiment, X is chloro, while in another embodiment X is bromo.

In one embodiment, each $R''$ is H, $R^z$ is H, X is chloro, and the compound of formula (II-Aii) is 5-(chloromethyl)tetrahydrofuran-2-carboxylic acid. Thus, in one embodiment, the compound of formula (II-Aii) is:

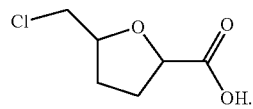

In another embodiment, each $R''$ is H, $R^z$ is H, X is bromo, and the compound of formula (II-Aii) is 5-(bromomethyl)tetrahydrofuran-2-carboxylic acid. Thus, in one embodiment, the compound of formula (II-Aii) is:

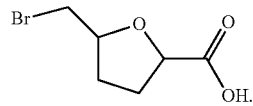

In other variations, $R^x$ is OC(O)$R^a$, and the compound of formula (II-ii) is a compound of formula (I-Bii):

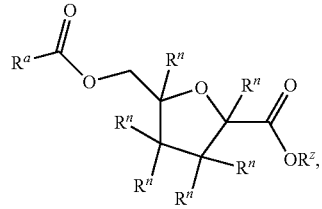

(II-Bii)

wherein:
  each $R''$ is independently H or alkyl;
  $R^z$ is H or alkyl; and
  $R^a$ is H, aliphatic or aromatic.

In some embodiments of the compound of formula (II-Bii), $R^a$ is aliphatic.

In one variation, each $R''$ is H, $R^z$ is H, $R^a$ is an aliphatic group, wherein the aliphatic group is linear $C_{11}$ alkyl, and the compound of formula (II-Bii) is 5-((dodecanoyloxy)methyl)tetrahydrofuran-2-carboxylic acid. Thus, in one variation, the compound of formula (II-Bii) is:

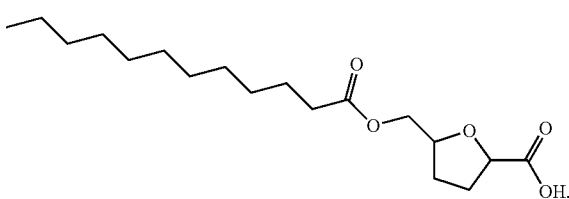 [SMILES: CCCCCCCCCCCC(=O)OCC1CCC(C(=O)O)O1]

In other variations of formula (II-ii), $R^x$ is $OR^b$, and the compound of formula (II-ii) is a compound of formula (II-Cii):

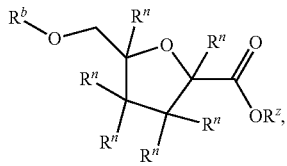

(II-Cii)

wherein:
each $R''$ is independently H or alkyl;
$R^z$ is H or aliphatic; and
$R^b$ is aliphatic.

For example, in one embodiment, $R^b$ is a linear alkyl, while in another embodiment, $R^b$ is an ether.

In one variation, each $R''$ is H, $R^z$ is H, $R^b$ is a polyethylene glycol methyl ether, and the compound of formula (II-Cii) is:

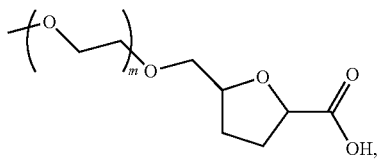

wherein m is an integer greater than 1.

Salts of Compounds of Formula (II)

In some variations, salts of the compounds of formula (II), including, for example, salts of halomethylfuroic and acyloxymethylfuroic compounds, may also be produced. It should be understood that salts of the compounds of formula (II) may include compositions with a charged compound of formula (II) and one or more counterions of opposite charge.

For example, in some variations, salts of the compounds of formula (II) may include compositions with a negatively charged compound of formula (II) and one or more positively charged counterions. Positively charged counterions may include, for example, Group I metal cations (such as $Na^+$, $K^+$, or $Li^+$), Group II metal cations (such as $Mg^{2+}$ or $Ca^{2+}$), polyatomic cations (such as $NH_4^+$), or other metal cations (such as $Cu^+$, $Cu^{2+}$, $Fe^{2+}$, $Fe^{3+}$, $Ag^+$, or $Al^{3+}$), or any combinations thereof.

In other variations, salts of the compounds of formula (II) may include compositions with a postively charged compound of formula (II) and one or more negatively charged counterions. Negatively charged counterions may include, for example, negatively charged halogen anions (such as $F^-$, $Cl^-$, $Br^-$, or $F^-$) or polyatomic anions (such as $CO_3^{2-}$, $HCO_3^-$, $HO^-$, $H_2PO_4^-$, $HPO_4^{2-}$, $PO_4^{3-}$, $NO_3^-$, $NO_2^-$, $CH_3OO^-$, or $HCOO^-$), or any combinations thereof.

It should further be understood that in some variations, a mixture of salts may be produced, depending on the oxidants used. For example, when one oxidant contains the Group I cation $Na^+$ and an additional oxidant contains the Group I cation $K^+$, a mixture of $Na^+$ and $K^+$ salts of the compound of formula (II) may be produced. For example, in one embodiment, one oxidant is $NaClO_2$, the additional oxidant is $KClO_2$, and a mixture of $Na^+$ and $K^+$ salts of the compound of formula (II) is produced.

In some variations, the salt of a compound of formula (II) is a compound of formula (IIX):

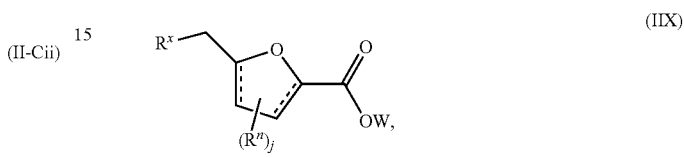

(IIX)

wherein:
$=\!=\!=$ is a double bond or a single bond;
j is 2 when $=\!=\!=$ is a double bond, or j is 6 when $=\!=\!=$ is a single bond;
each $R''$ is independently H or alkyl;
$R^x$ is halo, $OC(O)R^a$ or $OR^b$;
wherein $R^a$ is H, aliphatic or aromatic, and $R^b$ is aliphatic; and
W is a cation.

It should be understood that the cation W may vary depending on the oxidant used, other cations present during the reaction, and the reaction work-up.

In certain variations, W varies depending on the oxidant used. For example, in some embodiments, when $NaClO_2$ is used as the oxidant, W is $Na^+$. If a mixture of oxidants with different W is used, a mixture of compounds of formula (IIX) may be produced. For example, in one embodiment, one oxidant is $NaClO_2$, the additional oxidant is $KClO_2$, and a mixture of compounds of formula (IIX) is produced, wherein W is $Na^+$ in the first compound of formula (IIX), and W is $K^+$ in the additional compound of formula (IIX).

In other embodiments, W varies depending on other cations present during the reaction. It should be understood that other cations may include cations in the reaction mixture which were not derived from the oxidant. For example, one or more other cations may be included in the reaction mixture as part of salts, solvents, buffers, acids, bases, or other additional compounds. For example, in some embodiments, $NaClO_2$ is used as the oxidant, the reaction mixture includes a potassium buffer, and a compound of formula (IIX) is produced wherein W is $K^+$. In another embodiment, $NaClO_2$ is used as the oxidant, the reaction mixture includes an ammonium salt, and a compound of formula (IIX) is produced wherein W is $NH_4^+$. With reference again to FIG. 2A, in one variation of process 200, a salt buffer is included in the reaction mixture, and the compound of formula (II) produced is a compound of formula (IIX).

In still other embodiments, W varies depending on the type of reaction work-up used. The reaction work-up may include the addition of acids, bases, salts, solvents, or other compounds to the product mixture. For example, in one embodiment, the reaction work-up includes adding sodium hydroxide to the product mixture to isolate the compound of formula (IIX), wherein W is $Na^+$ With reference again to FIG. 2A, in some variations, process 200 includes additional steps of isolating the compound of formula (II) produced. In one such variation, process 200 includes adding one or more acids, bases, salts, solvents, or other compounds to the product mixture, and the compound of formula (II) is a compound of formula (IIX), wherein W is derived from the one or more acids, bases, salts, solvents, or other compounds.

In one variation, a compound of formula (I) is contacted by an oxidant according to the method described herein to produce a compound of formula (IIX), wherein:
the compound of formula (I) is:

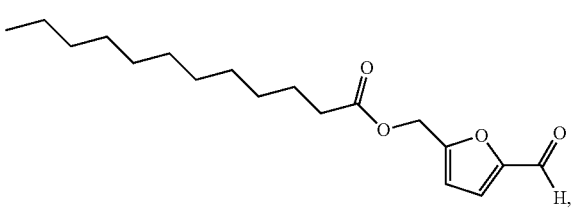

the oxidant is NaClO$_2$, and
the compound of formula (IIX) is:

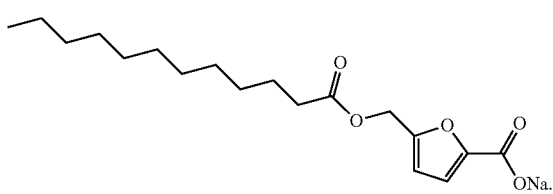

Thus, in one embodiment, the salt of the compound of formula (II) produced according to the methods described herein is the sodium salt of 5-(dodecanoyloxy)methyl-2-furoic acid (or sodium 5-((dodecanoyloxy)methyl)furanyl-2-carboxylate).

In one embodiment, the compound of formula (IIX) is the potassium salt of 5-(dodecanoyloxy)methyl-2-furoic acid, while in yet another embodiment, the salt is the lithium salt of 5-(dodecanoyloxy)methyl-2-furoic acid. In still another embodiment, a mixture of salts of 5-(dodecanoyloxy)methyl-2-furoic acid is produced.

In another variation, the compound of formula (I) is:

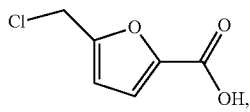

the oxidant is NaClO$_2$; and
the compound of formula (IIX) is:

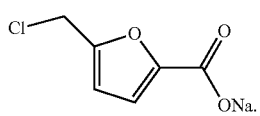

Thus, in one embodiment, the compound of formula (IIX) produced according to the methods described herein is the sodium salt of 5-chloromethyl-2-furoic acid. In another embodiment, the salt is the potassium salt of 5-chloromethyl-2-furoic acid, while in yet another embodiment, the salt is the lithium salt of 5-chloromethyl-2-furoic acid. In still another embodiment, a mixture of salts of 5-chloromethyl-2-furoic acid is produced.

It should be understood that while the salt of the compound of formula (II) is depicted as a monovalent salt above, polyvalent salts of the compound of formula (II) may also be produced by the methods described herein. For example, in certain embodiments, W is a cation with a charge of 2+, and the salt of the compound of formula (II) is:

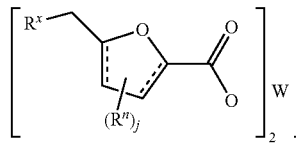

In other embodiments, W is a cation with a charge of 3+, and the salt of the compound of formula (II) is:

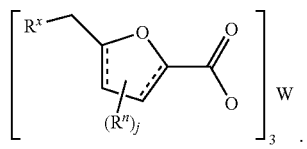

In still other embodiments, W is a cation with a charge of 4+, and the salt of the compound of formula (II) is:

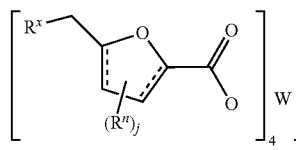

For example, in one variation, a compound of formula (I) is contacted by an oxidant according to the method described herein to produce the salt of a compound of formula (II), wherein:
the compound of formula (I) is:

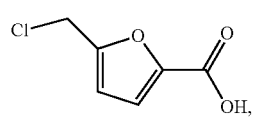

the oxidant is Ca(ClO$_2$)$_2$; and
the salt of the compound of formula (II) is:

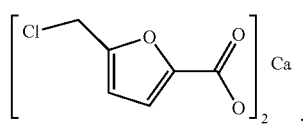

Thus, in one embodiment, the compound of formula (IIX) produced according to the methods described herein is the calcium salt of 5-chloromethyl-2-furoic acid.

In another variation, a compound of formula (I) is contacted by an oxidant according to the method described herein to produce the salt of a compound of formula (II), wherein:
the compound of formula (I) is:

[structure: 5-chloromethyl-2-furoic acid]

the oxidant is NaClO$_2$;
the compound of formula (I) is contacted by the oxidant in the presence of Mg$^{2+}$; and
the salt of the compound of formula (II) is:

[structure: magnesium salt of 5-chloromethyl-2-furoic acid]

Thus, in one embodiment, the compound of formula (IIX) produced according to the methods described herein is the magnesium salt of 5-chloromethyl-2-furoic acid.

Compounds of Formula (IIX-i)

In some variations, === is a double bond and j is 2, and the compound of formula (IIX) is a compound of formula (IIX-i):

[structure (IIX-i)]

wherein:
each R″ is independently H or alkyl;
R$^x$ is halo, OC(O)R$^a$ or OR$^b$;
wherein R$^a$ is H, aliphatic or aromatic, and R$^b$ is aliphatic; and
W is a cation.

In some variations of the methods described herein, === is a double bond, j is 2, R$^x$ is halo, and a compound of formula (I-Ai) is contacted by an oxidant to produce a salt of a compound of formula (II-Ai), wherein the salt is a compound of formula (IIX-Ai):

[structure (IIX-Ai)]

wherein:
each R″ is independently H or alkyl;
X is halo; and
W is a cation.

For example, in one embodiment, each R″ is H, X is chloro, W is Na$^+$, and the compound of formula (IIX-Ai) is the sodium salt of 5-chloromethylfuroic acid (or sodium 5-(chloromethyl)furan-2-carboxylate).

In other variations of the methods described herein, === is a double bond, j is 2, R$^x$ is —OC(O)R$^a$, and a compound of formula (I-Bi) is contacted by an oxidant to produce a salt of a compound of formula (II-Bi), wherein the salt is a compound of formula (IIX-Bi):

[structure (IIX-Bi)]

wherein:
each R″ is independently H or alkyl;
R$^a$ is H, aliphatic or aromatic; and
W is a cation.

For example, in one embodiment, each R″ is H, R$^a$ is a linear C$_{17}$ alkyl, W is Na$^+$, and the compound of formula (IIX-Bi) is the sodium salt of 5-(octadecanoyloxy)methyl-2-furoic acid (or sodium 5-((octadecanoyloxy)methyl)furan-2-carboxylate). In another embodiment, each R″ is H, R$^a$ is a linear C$_{11}$ alkyl, W is Na$^+$, and the compound of formula (IIX-Bi) is the sodium salt of 5-(dodecanoyloxy)methyl-2-furoic acid (or sodium 5-((dodecanoyloxy)methyl)furan-2-carboxylate).

In other variations of the methods described herein, === is a double bond, j is 2, R$^x$ is OR$^b$, and the compound of formula (IIX-i) is a compound of formula (IIX-Ci):

[structure (IIX-Ci)]

wherein:
each R″ is independently H or alkyl;
R$^b$ is aliphatic; and
W is a cation.

For example, in some variations, each R″ is H, R$^b$ is a polyethylene glycol methyl ether, W is Na$^+$, and the compound of formula (IIX-Ci) is:

[structure with PEG chain, ONa]

wherein m is an integer greater than 1.

Compounds of Formula (IIX-ii)

In other variations, === is a single bond and j is 6, and the compound of formula (IIX) is a compound of formula (IIX-ii):

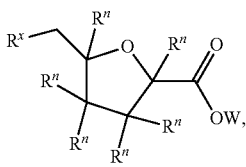
(IIX-ii)

wherein:
each $R^n$ is independently H or alkyl;
$R^x$ is halo, $OC(O)R^a$ or $OR^b$;
wherein $R^a$ is H, aliphatic or aromatic, and $R^b$ is aliphatic; and
W is a cation.

In some variations, $R^x$ is halo, and the compound of formula (IIX-ii) is a compound of formula (IIX-Aii):

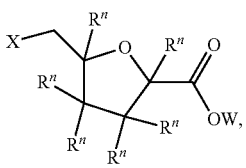
(IIX-Aii)

wherein:
each $R^n$ is independently H or alkyl;
X is halo; and
W is a cation.

In other variations, $R^x$ is $OC(O)R^a$, and the compound of formula (IIX-ii) is a compound of formula (IIX-Bii):

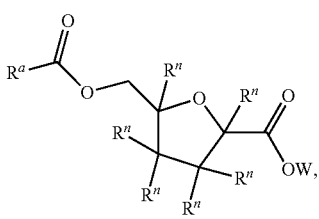
(IIX-Bii)

wherein:
each $R^n$ is independently H or alkyl;
$R^a$ is H, aliphatic or aromatic; and
W is a cation.

In other variations of formula (IIX-ii), $R^x$ is $OR^b$, and the compound of formula (IIX-ii) is a compound of formula (IIX-Cii):

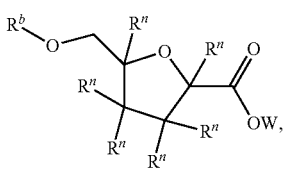
(IIX-Cii)

wherein:
each $R^n$ is independently H or alkyl;
$R^b$ is aliphatic; and
W is a cation.

It should be understood that while the compounds of formula (IIX), including formulae (IIX-Ai), (IIX-Bi), (IIX-Ci), (IIX-Aii), (IIX-Bii), and (IIX-Cii), are depicted with the moiety

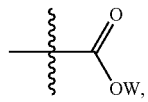

in some variations the compounds of formula (IIX) may be produced in solvated form, wherein the carboxylate anion and the cation are separated in solution.

Any of the variations of $R^x$, $R^n$, $R^a$, $R^b$ and X described herein with respect to the compounds of formulae (I), (I-i), (I-ii), (I-Ai), (I-Bi), (I-Ci), (I-Aii), (I-Bii), and (I-Cii) apply as if each were individually listed for $R^x$, $R^n$, $R^a$, $R^b$ and X of the compounds of formulae (I), (I-i), (I-ii), (I-Ai), (I-Bi), (I-Ci), (I-Aii), (I-Bii), and (I-Cii) and the compounds of formulae (II), (II-i), (II-ii), (II-Ai), (II-Bi), (II-Ci), (II-Aii), (II-Bii), (II-Cii), (IIX-i), (IIX-ii), (IIX-Ai), (II-Bi), (IIX-Ci), (IIX-Aii), (IIX-Bii) and (IIX-Cii), as applicable.

The furfuryl and tetrahydrofuranyl starting compounds may be converted to furoic and tetrahydrofuroic compounds in the presence of (i) water or alcohol, (ii) one or more of the following oxidants: halite compounds, halate compounds, halous acid compounds, halic acid compounds, or halogen dioxide compounds, or any combinations thereof.

Oxidants

The compounds of formula (I) may be converted to compounds of formula (II), or a salt thereof, in the presence of water or alcohol and one or more of the following oxidants: halite compounds, halate compounds, halous acid compounds, halic acid compounds, or halo dioxide compounds, or any combinations thereof.

The oxidants suitable for use in the methods herein are described in further detail below. It should generally be understood that the oxidants used may either be provided as a reagent that is obtained from any commercially available reagent or generated in situ by any methods known in the art. In some embodiments, one or more reagents are obtained from a commercial source. Combinations of the oxidants described herein may be used.

Halite Compounds

In some embodiments, the halite compound used has a formula of $W^b$-$O_2X^b$, wherein $W^b$ is a Group I cation and $X^b$ is halo. In some variations, $W^b$ is sodium, lithium or potassium. In one variation, $X^b$ is chloro. In another variation, $X^b$ is bromo.

In other embodiments, the halite compound used has a formula of $Z^b$—$(O_2X^b)_2$, wherein $Z^b$ is a Group II cation and $X^b$ is halo. In some variations, $Z^b$ is calcium or magnesium. In one variation, $X^b$ is chloro. In another variation, $X^b$ is bromo.

Suitable halite compounds may include, for example, sodium chlorite, lithium chlorite, potassium chlorite, magnesium chlorite, calcium chlorite, or sodium bromite.

The halite compounds used may be obtained from any commercially available sources or produced according to any suitable methods known in the art.

It should also generally be understood that when a halite compound having a Group I or Group II cation is used, the compound of formula (II) produced may be in the form of a salt. Thus, in some variations of the methods described herein, a compound of formula (IIX) is produced wherein W is $W^b$. In other variations, a compound of formula (IIX) is produced wherein W is $Z^b$.

For example, when sodium chlorite is used in combination with 5-chloromethylfurfural and water, the sodium salt of 5-chloromethyl-2-furoic acid may be produced. In another embodiment, when sodium chlorite is used in combination with 5-(dodecanoyloxy)methylfurfural, the sodium salt of 5-(dodecanoyloxy)methyl-2-furoic acid may be produced.

Halate Compounds

In some embodiments, the halate compound used has a formula of $W^d$-$O_3X^d$, wherein $W^d$ is a Group I cation and $X^d$ is halo. In some variations, $W^d$ is sodium, lithium or potassium. In one variation, $X^d$ is chloro. In another variation, $X^d$ is bromo.

In other embodiments, the halate compound used has a formula of $Z^d$—$(O_3X^d)_2$, wherein $Z^d$ is a Group II cation and $X^d$ is halo. In some variations, $Z^d$ is calcium or magnesium. In one variation, $X^d$ is chloro. In another variation, $X^d$ is bromo.

Suitable halate compounds may include, for example, sodium chlorate, potassium chlorate, lithium chlorate, calcium chlorate, magnesium chlorate, or sodium bromate.

The halate compounds used may be obtained from any commercially available sources or produced according to any suitable methods known in the art.

It should also generally be understood that when a halate compound having a Group I or Group II cation is used, the compound of formula (II) produced may be in the form of a salt. Thus, in some variations of the methods described herein, a compound of formula (IIX) is produced wherein W is $W^d$. In other variations, a compound of formula (IIX) is produced wherein W is $Z^d$.

For example, when sodium chlorate is used in combination with 5-chloromethylfurfural and water, the sodium salt of 5-chloromethyl-2-furoic acid may be produced. In another embodiment, when sodium chlorate is used in combination with 5-(octadecanoyloxy)methylfurfural, the sodium salt of 5-(octadecanoyloxy)methyl-2-furoic acid may be produced.

Halous Acid Compounds

In some embodiments, the halous acid compound used has a formula of $HX^bO_2$, wherein $X^b$ is halo. In one variation, $X^b$ is chloro. In another variation, $X^b$ is bromo.

Suitable halous acid compounds may include, for example, chlorous acid or bromous acid.

The halous acid compounds used may be obtained from any commercially available sources or produced according to any suitable methods known in the art.

Halic Acid Compounds

In some embodiments, the halic acid compound used has a formula of $HX^dO_3$, wherein $X^d$ is halo. In one variation, $X^d$ is chloro. In another variation, $X^d$ is bromo.

Suitable halic acid compounds may include, for example, chloric acid or bromic acid.

The halous acid compounds used may be obtained from any commercially available sources or produced according to any suitable methods known in the art.

Halo Dioxide Compounds

In some embodiments, the halo dioxide compound used has a formula of $X^cO_2$, wherein $X^c$ is halo. In one variation, $X^c$ is chloro. In another variation, $X^c$ is bromo.

Suitable halo dioxide compounds may include, for example, chlorine dioxide.

The halo dioxide compounds used may be obtained from any commercially available sources or produced according to any suitable methods known in the art. In some variations, the halo dioxide may be produced in situ by any suitable methods known in the art. For example, in some embodiments, chlorine dioxide is produced by combining sodium chlorite and an acid. In one embodiment, chlorine dioxide is produced by combining sodium chlorite and hydrochloric acid.

The various oxidants described herein may be used in combination with each other or with other compounds to convert a compound of formula (I), or a salt thereof, into a compound of formula (II), or a salt thereof.

In some variations of the methods described herein, the mole ratio of the one or more oxidants to the compound of formula (I) is between 0.1 and 4.0, between 0.5 and 3.0, between 0.5 and 2.5, between 1.0 and 2.0, or between 1.0 and 1.5.

Other Compounds

In other embodiments, an alkene, a peroxide or an organosulfur compound, or any combinations thereof, may be added to the reaction mixture. Organosulfur compounds include organic compounds with a carbon-sulfur bond. Without wishing to be bound by any theory, a hypohalite or a hypohalous acid may be produced in some variations of the methods described herein, and the addition of the alkene, peroxide or organosulfur compound to the reaction mixture may act as a hypohalite or hypohalous acid scavenger and increase the yield of the compound of formula (II) produced. In one embodiment, hydrogen peroxide is added to the reaction mixture. In another embodiment, the organosulfur compound dimethyl sulfoxide is added to the reaction mixture. In yet another embodiment, the organosulfur compound thiodiethanol is added to the reaction mixture.

In some variations, less than 1%, less than 5%, less than 10%, less than 15%, less than 20%, less than 25%, or less than 30% of hypohalite or hypohalous acid is present in the reaction mixture relative to the sum of the furan or tetrahydrofuran starting material and product compound of formula (II), by mole %.

Water or Alcohol

The compounds of formula (I), including, for example, halomethylfurfural or acyloxymethylfurfural starting compounds, may be converted to compounds of formula (II), including halomethylfuroic or acyloxymethylfuroic compounds, or salts thereof in the presence of (i) water or alcohol, and (ii) one or more oxidants.

It should be understood that when the furfural starting compound of formula (I) is combined with water and an oxidant, a halomethylfuroic acid or acyloxymethylfuroic acid compound of formula (II) is produced, wherein $R^z$ is H; or a compound of formula (IIX) is produced, wherein W is a cation. In some variations, a mixture of compounds of formula (II), wherein $R^z$ is H; and compounds of formula (IIX), wherein W is a cation, may be produced and/or isolated.

When the furfural starting compound of formula (I) is combined with an alcohol and an oxidant, a halomethylfuroic ester or acyloxymethylfuroic ester compound of formula (II) is produced, wherein $R^z$ is alkyl. Any suitable alkyl alcohol may be used to produce the compound of formula (II). It should be understood that the alkyl group of $R^z$ in the compound of formula (II) is the same alkyl group of the alkyl alcohol. For example, in one embodiment, 5-chloromethylfurfural is combined with methanol and an oxidant to produce methyl 5-(chloromethyl)furan-2-carboxylate.

For example, with reference again to FIG. 1B, process 120 depicts an exemplary process to produce compound 130, one example of a compound of formula (II), wherein $R^z$ is alkyl. Compound 122 is combined with oxidant compound 124, alcohol 126, and dimethyl sulfoxide 128 to produce compound 130, wherein alcohol 126 is methanol and $R^z$ is methyl.

With reference to FIG. 2B, process 220 depicts an exemplary process to produce compound 230, one example of a compound of formula (II) wherein $R^z$ is alkyl. Compound 222 is combined with oxidant compound 224, alcohol 226, and dimethyl sulfoxide 228 to produce compound 230, wherein alcohol 226 is ethanol and $R^z$ is ethyl.

It should be understood that while process 120 depicts the use of methanol 126, and process 220 depicts the use of ethanol 226, any suitable alcohol may be used in the methods described herein to produce a compound of formula (II) wherein $R^z$ is alkyl. For example, in one variation of process 220, alcohol 226 is tert-butanol and compound 230 is produced wherein $R^z$ is tert-butyl.

In some variations, wherein a compound of formula (I-Ai) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula (I-Ai) is hydrolyzed to a hydroxymethyl group. For example, in one embodiment, 5-chloromethylfurfural is combined with water and an oxidant, and less than 10% of the 5-chloromethylfurfural is hydrolyzed to 5-hydroxymethylfurfural.

In some variations, wherein a compound of formula (I-Aii) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula (I-Aii) is hydrolyzed to a hydroxymethyl group.

In some variations, wherein a compound of formula (I-Ai) is combined with one or more oxidants and an alcohol, less than 50 mole %, less than 40 mole %, less than 30 mole %, less than 20 mole %, less than 15 mole %, less than 10 mole %, or less than 5 mole % of the halomethyl group of the compound of formula (I-Ai) undergoes alcoholysis to an ether group. For example, in one embodiment, 5-chloromethylfurfural is combined with methanol and an oxidant, and less than 10% of the 5-chloromethylfurfural undergoes alcoholysis to the methyl ether of 5-hydroxymethylfurfural (5-(methoxymethyl)furan-2-carbaldehyde).

In some variations, wherein a compound of formula (I-Aii) is combined with one or more oxidants and an alcohol, less than 50 mole %, less than 40 mole %, less than 30 mole %, less than 20 mole %, less than 15 mole %, less than 10 mole %, or less than 5 mole % of the halomethyl group of the compound of formula (I-Aii) undergoes alcoholysis to an ether group.

In some variations, wherein a compound of formula (I-Ai) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula (II-Ai) is hydrolyzed to a hydroxymethyl group. For example, in one embodiment, 5-chloromethylfurfural is combined with water and an oxidant to produce 5-chloromethyl-2-furoic acid, and less than 10% of the 5-chloromethyl-2-furoic acid is hydrolyzed to 5-hydroxymethyl-2-furoic acid. In some variations, wherein a compound of formula (I-Ai) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula (I-Ai) is converted to a hydroxymethyl group.

In some variations, wherein a compound of formula (I-Aii) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula II-Aii) is hydrolyzed to a hydroxymethyl group.

In some variations, wherein a compound of formula (I-Ai) is combined with one or more oxidants and an alcohol, less than 50 mole %, less than 40 mole %, less than 30 mole %, less than 20 mole %, less than 15 mole %, less than 10 mole %, or less than 5 mole % of the halomethyl group of the compound of formula (II-Ai) undergoes alcoholysis to an ether group. For example, in one embodiment, 5-chloromethylfurfural is combined with methanol and an oxidant to produce methyl 5-(chloromethyl)furan-2-carboxylate, and less than 10% of the methyl 5-(chloromethyl)furan-2-carboxylate undergoes alcoholysis to methyl 5-(methoxymethyl)furan-2-carboxylate. In some variations, wherein a compound of formula (I-Ai) is combined with one or more oxidants and an alcohol, less than 50 mole %, less than 40 mole %, less than 30 mole %, less than 20 mole %, less than 15 mole %, less than 10 mole %, or less than 5 mole % of the halomethyl group of the compound of formula (I-Ai) undergoes alcoholysis to an ether group.

In some variations, wherein a compound of formula (I-Aii) is combined with one or more oxidants and an alcohol, less than 50 mole %, less than 40 mole %, less than 30 mole %, less than 20 mole %, less than 15 mole %, less than 10 mole %, or less than 5 mole % of the halomethyl group of the compound of formula (II-Aii) undergoes alcoholysis to an ether group. In some variations, wherein a compound of formula (I-Aii) is combined with one or more oxidants and an alcohol, less than 50 mole %, less than 40 mole %, less than 30 mole %, less than 20 mole %, less than 15 mole %, less than 10 mole %, or less than 5 mole % of the halomethyl group of the compound of formula (I-Aii) undergoes alcoholysis to an ether group In some variations, wherein a compound of formula (I-Ai) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula (IIX-Ai) is hydrolyzed to a hydroxymethyl group. For example, in one embodiment, 5-chloromethylfurfural is combined with water and an oxidant to produce the sodium salt of 5-chloromethyl-2-furoic acid, and less than 10% of the sodium salt of 5-chloromethyl-2-furoic acid is hydrolyzed to the sodium salt of 5-hydroxymethyl-2-furoic acid.

In other variations, wherein a compound of formula (I-Aii) is combined with one or more oxidants and water, less than 50 mole %, less than 40 mole %, less than 30 mole %, less than 20 mole %, less than 15 mole %, less than 10 mole %, or less than 5 mole % of the halomethyl group of the compound of formula (IIX-Aii) is hydrolyzed to a hydroxymethyl group.

It has been observed that, using the methods described herein, oxidation of the starting compound of formula (I-Ai) or formula (I-Aii) in the aqueous phase is unexpectedly faster than solvolytic conversion of the halomethyl group to a hydroxymethyl group or an ether group in the starting compound of formula (I-Ai) or formula (I-Aii). It has also been observed that when compounds of formula (II-Ai), (II-Aii), (IIX-Ai) or (IIX-Aii) are produced according to the methods described herein, an unexpectedly low percentage of the halomethyl group is solvolyzed to a hydroxymethyl group or an ether group.

Phase Transfer Catalysts

In some variations of the methods described herein, a phase transfer catalyst is added to the reaction mixture. It should generally be understood that the phase transfer catalysts used may either be provided as a reagent that can be obtained from any commercially available reagent or generated in situ by any methods known in the art. In some variations, one or more phase transfer catalysts may be a commercially available reagent.

In some variations, the phase transfer catalyst has a cation and an anion. In certain variations, the cation is tetraalkyl ammonium or tetraalkyl phosphonium. It should generally be understood that "tetraalkyl" refers to a moiety with four alkyl groups that may be the same or different. For example, tetraalkyl ammonium may be methyltributylammonium, where one of the four alkyl groups is methyl and the remaining three alkyl groups are butyl. In certain variations, the anion is a halide or a bisulfate.

Suitable phase transfer catalysts include, for example, methyltributylammonium chloride.

In some embodiments of the methods described herein, the compound of formula (II) is produced in a biphasic reaction mixture, wherein at least a portion of the compound of formula (I) is present in the organic phase, and at least a portion of the oxidant(s) is present in the aqueous phase. In some variations of the methods, without wishing to be bound by any theory, the addition of a phase transfer catalyst may cause at least a portion of the oxidant(s) to shift into the organic phase, and react with the compound of formula (I) in the organic phase. In other variations of the methods, without wishing to be bound by any theory, the addition of a phase transfer catalyst may cause at least a portion of the oxidant(s) and compound of formula (I) to interact at the interface of the organic and aqueous layers of the biphasic reaction mixture.

Solvent

The methods described herein may, in some variations, be performed in the absence of solvent (i.e., neat). In other variations, a solvent is used. Any combinations of suitable solvents may also be used.

In some variations, the solvent is or includes an organic solvent. In some variations, the solvent is selected to dissolve, or at least partially dissolve, the compound of formula (I). In some variations, the solvent is selected to dissolve, or at least partially dissolve, the one or more oxidants. In certain variations, the solvent may also have at least partial miscibility with the water or alcohol. In other variations, the solvent will be fully miscible with the water or alcohol.

In certain variations, the solvent is a polar solvent, and is partially miscible with the water or alcohol.

In some embodiments, the solvent is an ether (for example, tetrahydrofuran) or a carboxylic acid (for example, acetic acid).

In some embodiments, the solvent is acetic acid, dimethyl sulfoxide, dimethoxyethane, tetrahydrofuran, or acetonitrile, or any combinations thereof.

In other variations, the solvent may have limited solubility with the water or alcohol, and may form a biphasic reaction mixture.

Reaction pH

In some variations of the methods described herein, the method includes adjusting and/or maintaining the pH of the reaction mixture. For example, in some variations, the pH of the reaction mixture is adjusted to and/or maintained at a pH of between 0 and 7, or between 0 and 5, or between 0 and 4, or between 1 and 3, or between 1.5 and 2.5. In one embodiment, the pH of the reaction mixture is adjusted to and/or maintained at a pH of between 1.5 and 2.5. In other embodiments, the compound of formula (II) is produced at a pH of between 0 and 7, or between 0 and 5, or between 0 and 4, or between 1 and 3, or between 1.5 and 2.5. In one embodiment, the compound of formula (II) is produced at a pH of between 1.5 and 2.5.

In some embodiments, a buffer may be used to control the pH of the reaction.

For example, in some variations, a phosphate buffer may be used.

Any combinations of suitable buffers may also be used. The buffers may be obtained from any commercially available sources or produced according to any suitable methods known in the art.

In other embodiments, an acid or a base may be added to the reaction mixture to adjust the pH of the reaction. For example, in some variations, hydrochloric acid may be used to adjust the pH of the reaction.

Reactors and Vessels

The methods described herein may be carried out batchwise or continuously. The methods described herein may be performed in any suitable reactors, including open or closed reactors, which can contain the chemical reactions described herein. Suitable reactors may include, for example, a fed-batch stirred reactor, a batch stirred reactor, a continuous flow stirred reactor, a continuous plug-flow column reactor, an attrition reactor, fixed bed reactor and a fluidized bed reactor. The reactor may include a continuous mixer, such as a screw mixer.

Additionally, the reactor may allow for addition and removal of certain components in the reaction mixture. For example, the reactor can have one or more outlets to add additional solvent or acid, or to remove the organic or aqueous phase from the reaction mixture. In some embodiments, the reactor may have one or more outlets that connecting the reactor to an isolation vessel, where the organic phase can be transferred from the reactor to the isolation vessel.

The reactors and vessels used herein may be generally made up of materials that are capable of withstanding the physical and chemical forces exerted during the methods described herein. In some embodiments, such materials used are capable of tolerating high concentrations of strong liquid acids. For example, the reactors and vessels may be made up of glass, metal or Pyrex®.

Isolation and Purification

The methods described herein may further include isolating and/or purifying the compounds of formula (II), including, for example, halomethylfuroic or acyloxymethylfuroic compounds, or salts thereof produced. Any methods known in the art may be employed to isolate and/or purify the compounds of formula (II), or the salt thereof. For example, the compound of formula (II), or the salt thereof, may be isolated from the reaction mixture using a crystallizer, a filter, or a centrifuge.

In some variations, the compound of formula (II) is isolated as a solid. In certain variations, the compound of formula (II) is isolated by liquid-liquid extraction. For example, in one embodiment, the compound of formula (II) is produced in a monophasic reaction mixture; an extractant solvent that is at least partially immiscible with the reaction mixture is added, to form a biphasic liquid-liquid extraction system with a reaction phase and an extract phase; at least a portion of the compound of formula (II) in the reaction phase shifts to the extractant phase; and at least a portion of the extractant phase is removed to isolate the compound of formula (II). In certain embodiments, the compound of formula (II) is produced in a biphasic reaction mixture, and isolated by liquid-liquid extraction.

Any suitable extractant solvent may be used, including, for example, haloalkyl solvents. In some embodiments, the extractant solvent is dichloromethane or dichloroethane, or a combination thereof.

In certain variations, compound of formula (II) is produced in a biphasic reaction mixture, the aqueous phase is separated from the organic phase of the biphasic reaction mixture, and the compound of formula (II) is isolated from the organic phase of the reaction mixture.

It should be understood that in certain variations, the compound of formula (II), or the salt thereof, is not isolated and/or purified, and may be further used in one or more downstream reactions described herein.

Yield, Conversion and Selectivity

The yield of a product takes into account the conversion of the starting materials into the product, and the selectivity for the product over other products that may be formed.

The difference between yield, conversion and selectivity is explained in the examples provided herein. For example, with respect to the reaction of producing a compound of formula (II), or a salt thereof, by combining a compound of formula (I) with an oxidant and water or alcohol, the reaction can be generalized as follows, where "A" represents the moles of the compound of formula (I); "B" represents the moles of the oxidant; "W" represents the moles of the water or alcohol; and "C" represents the moles of the compound of formula (II), or the salt thereof, produced; and "a", "b", "w", and "c" are stoichiometric coefficients.

$$aA + bB + wW \rightarrow cC$$

It should be understood that at the equation above only illustrates the production of (II), and that the equation may be modified if one or more side products are formed. Conversion of A is the percentage of reactant A that has been consumed during the reaction shown above, as expressed by the following equation:

$$\% \text{ Conversion} = \left[\frac{Ao - Af}{Ao}\right] \times 100\%,$$

where $A_o$ is the initial number of moles of reactant A; and $A_f$ is the final number of moles of reactant A.

Selectivity is the stoichiometrically relative amount of product C produced from the converted amount of reactant A, as expressed as a percentage by the following equation:

$$\text{Selectivity (\%)} = \left[\frac{Cf * \frac{a}{c}}{Ao - Af}\right] \times 100\%,$$

where $A_o$ is the starting moles of reactant A; $A_f$ is the final number of moles of reactant A; and $C_f$ is the number of moles of product C. In some embodiments where "a/c"=1, and the equation can be simplified to:

$$\text{Selectivity (\%)} = \left[\frac{Cf}{Ao - Af}\right] \times 100\%.$$

The yield of product C is the percentage of reactant A that is converted into product C, as expressed by the following equation:

Yield (%)=[Conversion (%)]×[Selectivity (%)]

In certain embodiments, the methods described herein have a yield for the compound of formula (II), or a salt thereof, of at least 10%, at least 15%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% and 100%, between 10% and 90%, between 15% and 100%, between 15% and 90%, between 20% and 80%, between 30% and 80%, between 40% and 80%, between 50% and 80%, or between 60% and 80% by weight.

In certain embodiments, the methods described herein have a selectivity for the compound of formula (II), or a salt thereof, of at least 10%, at least 20%, at least 30%, at least 40%, at least 50%, at least 60%, at least 70%, at least 80%, at least 90%, or at least 99%. In other embodiments, the selectivity is between 40% and 99%, between 40% and 95%, between 40% and 90%, between 40% and 80%, between 50% and 99%, between 50% and 95%, between 50% and 90%, between 50% and 80%, between 60% and 99%, between 60% and 95%, between 60% and 90%, between 60% and 80%, between 70% and 99%, between 70% and 95%, between 70% and 90%, or between 70% and 80%.

Compounds of Formulae (II-1), (II-2), and (II-3)

Provided herein are also compounds of formula (II-1), or a salt thereof:

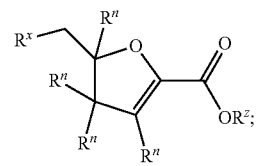

(II-1)

wherein:
each $R^n$ is independently H or alkyl;
$R^x$ is halo, OC(O)$R^a$ or O$R^b$;
wherein $R^a$ is H, aliphatic or aromatic, and $R^b$ is aliphatic; and
$R^z$ is H or aliphatic.

Provided herein are also compounds of formula (II-2), or a salt thereof:

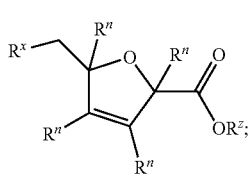

(II-2)

wherein:
each $R^n$ is independently H or alkyl;
R' is halo, OC(O)$R^a$ or O$R^b$;
wherein $R^a$ is H, aliphatic or aromatic, and $R^b$ is aliphatic; and
$R^z$ is H or aliphatic.

Provided herein are also compounds of formula (II-3), or a salt thereof:

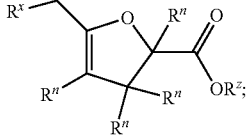

(II-3)

wherein:
each $R^n$ is independently H or alkyl;
$R'$ is halo, $OC(O)R^a$ or $OR^b$;
wherein $R^a$ is H, aliphatic or aromatic, and $R^b$ is aliphatic; and
$R^z$ is H or aliphatic.

Provided herein are also methods of producing compounds of formula (II-1), or a salt thereof, from compounds of formula (I-1), using any of the reactants and conditions described above, wherein the compound of formula (I-1) is:

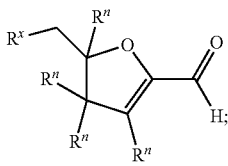

(I-1)

wherein:
each $R^n$ is independently H or alkyl;
$R^x$ is halo, $OC(O)R^a$ or $OR^b$;
wherein $R^a$ is H, aliphatic or aromatic, and $R^b$ is aliphatic.

Provided herein are also methods of producing compounds of formula (II-2), or a salt thereof, from compounds of formula (I-2), using any of the reactants and conditions described above, wherein the compound of formula (I-2) is:

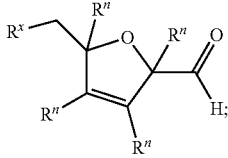

(I-2)

wherein:
each $R^n$ is independently H or alkyl;
$R^x$ is halo, $OC(O)R^a$ or $OR^b$;
wherein $R^a$ is H, aliphatic or aromatic, and $R^b$ is aliphatic.

Provided herein are also methods of producing compounds of formula (II-3), or a salt thereof, from compounds of formula (I-3), using any of the reactants and conditions described above, wherein the compound of formula (I-3) is:

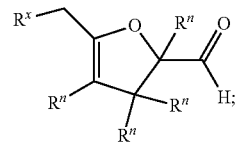

(I-3)

wherein:
each $R^n$ is independently H or alkyl;
$R^x$ is halo, $OC(O)R^a$ or $OR^b$;
wherein $R^a$ is H, aliphatic or aromatic, and $R^b$ is aliphatic; and
$R^z$ is H or aliphatic.

For example, in some embodiments, the compound of formula (II-1), or a salt thereof, is produced by combining a compound of formula (I-1) with an oxidant as described herein. In certain embodiments, the compound of formula (II-2), or a salt thereof, is produced by combining a compound of formula (I-2) with an oxidant as described herein. In yet other embodiments, the compound of formula (II-3), or a salt thereof, is produced by combining a compound of formula (I-3) with an oxidant as described herein. In certain embodiments, the oxidant is a compound of formulae $W^b$-$O_2X^b$, $Z^b$—$(O_2X^b)_2$, $W^d$-$O_3X^d$, $Z^d$—$(O_3X^d)_2$, $HX^dO_2$, $HX^dO_3$, or $X^cO_2$, or a combination thereof.

Any of the oxidants described herein may be used to produce the compounds of formulae (II-1), (II-2), or (II-3) from compounds of formulae (I-1), (I-2), or (I-3). In some variations, the oxidant is: a compound of formula $W^b$-$O_2X^b$, wherein $W^b$ is a Group I cation and $X^b$ is halo; $W^d$-$O_3X^d$, wherein $W^d$ is a Group I cation and $X^d$ is halo; $HX^bO_2$, wherein $X^b$ is halo; $HX^dO_3$, wherein $X^d$ is halo; or $X^cO_2$, wherein $X^c$ is halo.

It should generally be understood that any of the variations for $R^x$, $R^a$, $R^b$, $R^n$ and $R^z$ described herein may be combined the same as if each and every combination of the variables were specifically and individually listed for formulae (I-1), (I-2), (I-3), (II-1), (II-2), and (II-3), as applicable. It should further be generally understood that any of the variations for $W^b$, $W^d$, $X^b$, $X^c$, $X^d$, $Z^b$, and $Z^d$ described herein may be combined the same as if each and every combination of the variables were specifically and individually listed for the compounds of formulae $W^b$-$O_2X^b$, $Z^b$—$(O_2X^b)_2$, $W^d$-$O_3X^d$, $Z^d$—$(O_3X^d)_2$, $HX^bO_2$, $HX^dO_3$, or $X^cO_2$, as applicable.

In other aspects, provided herein are also compositions that include: a compound of Formula (II-1) and an oxidant, wherein the oxidant is a compound of formula: $W^b$-$O_2X^b$, $Z^b$—$(O_2X^b)_2$, $W^d$-$O_3X^d$, $Z^d$—$(O_3X^d)_2$, $HX^bO_2$, $HX^dO_3$, or $X^cO_2$; a compound of Formula (II-2) and an oxidant, wherein the oxidant is a compound of formula: $W^b$-$O_2X^b$, $Z^b$—$(O_2X^b)_2$, $W^d$-$O_3X^d$, $Z^d$—$(O_3X^d)_2$, $HX^bO_2$, $HX^dO_3$, or $X^cO_2$; or a compound of Formula (II-3) and an oxidant, wherein the oxidant is a compound of formula: $W^b$-$O_2X^b$, $Z^b$—$(O_2X^b)_2$, $W^d$-$O_3X^d$, $Z^d$—$(O_3X^d)_2$, $HX^bO_2$, $HX^dO_3$, or $X^cO_2$; or any combinations thereof.

Downstream Products

In some embodiments, the compound of formula (II), or a salt thereof, produced according to the methods described herein, may be suitable for use as a feedstock to produce other chemicals.

In some embodiments, the compound of formula (II), or a salt thereof, produced according to the methods described herein, may be suitable for use as a surfactant or in the production of a surfactant. The compound of formula (II), or a salt thereof, produced according to the methods described herein, may be suitable for use as a surfactant in the manufacture of or inclusion in fabric softeners, household cleaning products, laundry detergents, and personal care products. In some embodiments, the compound of formula (II), or a salt thereof, produced according to the methods described herein may be suitable for use in the production of a surfactant.

In some embodiments, the compound of formula (II), or salt thereof, produced according to the methods described herein may be suitable for use in the production of compounds other than surfactants.

It should generally be understood that any of the variations for $R^x$, $R^a$, $R^b$, $R^n$, $R^z$, X and W described herein may be combined the same as if each and every combination of the variables were specifically and individually listed for formulae (I), (I-i), (I-ii), (I-Ai), (I-Aii), (I-Bi), (I-Bii), (I-Ci), (I-Cii), (II), (II-i), (II-ii), (II-Ai), (II-Aii), (II-Bi), (II-Bii), (II-Ci), (II-Cii), (IIX), (IIX-i), (IIX-ii), (IIX-Ai), (IIX-Aii), (IIX-Bi), (IIX-Bii), (IIX-Ci), and (IIX-Cii), as applicable.

It should be understood that reference to "between" two values or parameters herein includes (and describes) embodiments that include those two values or parameters per se. For example, description referring to "between x and y" includes description of "x" and "y" per se.

It should also be understood that some of the chemical compounds described herein may be described using one or more chemical names. For example, 5-bromomethylfurfural may also be called 5-(bromomethyl)furan-2-carbaldehyde; 5-(dodecanoyloxy)methylfurfural may also be called (5-formylfuran-2-yl)methyl dodecanoate; and 5-chloromethyl-2-furoic acid may also be called 5-(chloromethyl)furan-2-carboxylic acid.

Enumerated Embodiments

The following enumerated embodiments are representative of some aspects of the invention.

1. A method of producing a compound of formula (II), or a salt thereof, comprising combining a compound of formula (I) with an oxidant to produce the compound of formula (II), or a salt thereof, wherein:
the compound of formula (I) is:

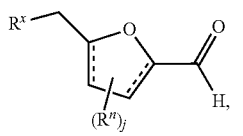
(I)

=== is a double bond or a single bond;
j is 2 when === is a double bond, or j is 6 when === is a single bond;
each $R^n$ is independently H or alkyl;
$R^x$ is halo, OC(O)$R^a$ or O$R^b$;
wherein $R^a$ is H, aliphatic or aromatic, and $R^b$ is aliphatic; and
the compound of formula (II) is:

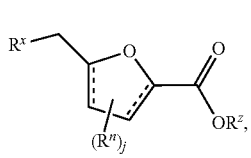
(II)

wherein $R^x$, $R^n$, j and === are as defined for formula (I); and
$R^z$ is H or aliphatic; and
the oxidant is:
(i) a compound of formula $W^b$-$O_2X^b$, wherein $W^b$ is a Group I cation and $X^b$ is halo;
(ii) $W^d$-$O_3X^d$, wherein $W^d$ is a Group I cation and $X^d$ is halo;
(iii) $HX^bO_2$, wherein $X^b$ is halo;
(iv) $HX^dO_3$, wherein $X^d$ is halo; or
(v) $X^cO_2$, wherein $X^c$ is halo.

2. The method of embodiment 1, wherein the compound of formula (II), or a salt thereof, is produced at a yield of at least 50%.

3. The method of embodiment 1 or 2, wherein === is a double bond and j is 2.

4. The method of embodiment 1 or 2, wherein === is a single bond and j is 6.

5. The method of any one of embodiments 1 to 4, wherein $R^x$ is halo.

6. The method of any one of embodiments 1 to 4, wherein $R^x$ is OC(O)$R^a$, wherein $R^a$ is H, aliphatic or aromatic.

7. The method of any one of embodiments 1 to 4, wherein $R^x$ is O$R^b$, wherein $R^b$ is aliphatic.

8. The method of any one of embodiments 1 to 7, wherein $R^z$ is H.

9. The method of any one of embodiments 1 to 7, wherein $R^z$ is aliphatic.

10. The method of any one of embodiments 1 to 9, wherein the compound of formula (I) and the oxidant are further combined with solvent.

11. The method of embodiment 10, wherein the solvent comprises an organic solvent.

12. The method of embodiment 11, wherein the solvent comprises acetic acid, dimethyl sulfoxide, dimethoxyethane, tetrahydrofuran, or acetonitrile, or any combinations thereof.

13. The method of any one of embodiments 1 to 12, wherein the compound of formula (I) and the oxidant are further combined with an alkene, a peroxide or an organosulfur compound, or any combinations thereof.

14. The method of embodiment 13, wherein the organosulfur compound is dimethyl sulfoxide or thiodiethanol.

15. The method of any one of embodiments 1 to 14, wherein the compound of formula (I) and the oxidant are further combined with a buffer.

16. The method of embodiment 15, wherein the buffer is a phosphate buffer.

17. The method of any one of embodiments 1 to 16, wherein the compound of formula (I) and the oxidant are further combined with an acid.

18. The method of embodiment 17, wherein the acid is hydrochloric acid.

19. The method of any one of embodiments 1 to 18, wherein the compound of formula (I) and the oxidant are combined with water to form a reaction mixture, wherein the reaction mixture has a pH; and
wherein the method comprises adjusting the pH of the reaction mixture to a pH of between 0 and 5.

20. The method of any one of embodiments 1 to 19, wherein the mole ratio of the oxidant to the compound of formula (I) is between 0.1 and 4.0.

21. The method of any one of embodiments 1 to 20, wherein the compound of formula (II), or a salt thereof, is produced in a one-pot synthesis.

22. The method of any one of the embodiments 1 to 21, wherein the compound of formula (II), or a salt thereof, is 5-(chloromethyl)furan-2-carboxylic acid, or a salt thereof.

23. The method of any one of the embodiments 1 to 22, wherein the compound of formula (I) is 5-chloromethylfurfural.

24. The method of any one of embodiments 1 to 23, wherein the compound of formula (II), or a salt thereof, is produced at a pH between 0 and 5.

25. The method of any one of embodiments 1 to 24, further comprising isolating the compound of formula (II), or a salt thereof, produced.

26. The method of embodiment 25, wherein the isolating comprises liquid-liquid extraction.

27. The method of embodiment 26, wherein the liquid-liquid extraction is performed with a haloalkyl solvent.

28. The method of embodiment 27, wherein the haloalkyl solvent comprises dichloromethane, chloroform, or dichloroethane, or any combinations thereof.

29. The method of any one of embodiments 1 to 28, wherein R' is halo and the compound of formula (I) comprises a halomethyl group, wherein less than 50% of the halomethyl group of the compound of formula (I) is hydrolyzed to a hydroxymethyl group.

30. The method of any of embodiments 1 to 29, wherein the compound of formula (II), or a salt thereof, is a solid.

31. A method of producing a halomethylfuroic acid, or a salt thereof, comprising combining a halomethylfurfural and an oxidant to produce a halomethylfuroic acid, or a salt thereof, wherein the oxidant is:
(i) a compound of formula $W^b\text{-}O_2X^b$, wherein $W^b$ is a Group I cation and $X^b$ is halo;
(ii) $W^d\text{-}O_3X^d$, wherein $W^d$ is a Group I cation and $X^d$ is halo;
(iii) $HX^bO_2$, wherein $X^b$ is halo;
(iv) $HX^dO_3$, wherein $X^d$ is halo; or
(v) $X^cO_2$, wherein $X^c$ is halo.

32. The method of embodiment 31, wherein the halomethylfurfural and the oxidant are further combined with water.

33. The method of embodiment 31, wherein the halomethylfuroic acid is produced at a yield of at least 50%.

34. The method of any one of embodiments 31 to 33, wherein the compound of formula $W^b\text{-}O_2X^b$ is $NaClO_2$.

35. The method of embodiment 31, wherein the compound of formula $HX^bO_2$ is $HClO_2$.

36. The method of embodiment 31, wherein the compound of formula $X^cO_2$ is $ClO_2$.

37. The method of any one of embodiments 31 to 33, wherein $W^b$ or $W^d$ is sodium, potassium, or lithium.

38. The method of any one of embodiments 31 to 37, wherein $X^b$, $X^c$, or $X^d$ is chloro.

39. The method of any one of embodiments 31 to 38, wherein the halomethylfurfural and the oxidant are further combined with solvent.

40. The method of embodiment 39, wherein the solvent comprises an organic solvent.

41. The method of embodiment 40, wherein the solvent comprises acetic acid, dimethyl sulfoxide, dimethoxyethane, tetrahydrofuran, or acetonitrile, or any combinations thereof.

42. The method of any one of embodiments 31 to 41, wherein the halomethylfurfural and the oxidant are further combined with an alkene, a peroxide or an organosulfur compound, or any combinations thereof.

43. The method of embodiment 42, wherein the organosulfur compound is dimethyl sulfoxide or thiodiethanol.

44. The method of any one of embodiments 31 to 43, wherein the halomethylfurfural and the oxidant are further combined with a buffer.

45. The method of embodiment 44, wherein the buffer is a phosphate buffer.

46. The method of any one of embodiments 31 to 45, wherein the halomethylfurfural and the oxidant are further combined with an acid.

47. The method of embodiment 46, wherein the acid is hydrochloric acid.

48. The method of any one of embodiments 31 to 47, wherein the halomethylfurfural and the oxidant are combined with water to form a reaction mixture, wherein the reaction mixture has a pH; and
wherein the method comprises adjusting the pH of the reaction mixture to a pH of between 0 and 5.

49. The method of any one of embodiments 31 to 48, wherein the mole ratio of the oxidant to the halomethylfurfural is between 0.1 and 4.0.

50. The method of any one of embodiments 1 to 31, or 33 to 49, wherein the oxidant is chlorous acid or chlorine dioxide, further comprising:
producing hypochlorous acid from the chlorous acid or chlorine dioxide, and
removing the hypochlorous acid produced.

51. The method of embodiment 50, wherein the removing is performed with an alkene, a peroxide or an organosulfur compound, or any combinations thereof.

52. The method of embodiment 51, wherein the organosulfur compound is dimethyl sulfoxide or thiodiethanol, or a combination thereof.

53. The method of embodiment 50 or 51, wherein less than 5 wt % of sodium hypochlorite is present relative to the oxidant.

54. The method of any one of the preceding embodiments, wherein the oxidant is produced in situ.

55. The method of embodiment 54, wherein the oxidant is produced in situ from sodium halite and an acid.

56. The method of any one of embodiments 31 to 55, wherein the halomethylfuroic acid, or a salt thereof, is produced in a one-pot synthesis.

57. The method of any one of the embodiments 31 to 56, wherein the halomethylfuroic acid, or a salt thereof, is 5-(chloromethyl)furan-2-carboxylic acid, or a salt thereof.

58. The method of any one of the embodiments 31 to 57, wherein the halomethylfurfural is 5-chloromethylfurfural.

59. The method of any one of embodiments 31 to 58, wherein the halomethylfuroic acid, or a salt thereof, is produced at a pH between 0 and 5.

60. The method of any one of embodiments 31 to 59, further comprising isolating the halomethylfuroic acid, or a salt thereof, produced.

61. The method of embodiment 60, wherein the isolating comprises liquid-liquid extraction.

62. The method of embodiment 61, wherein the liquid-liquid extraction is performed with a haloalkyl solvent.

63. The method of embodiment 62, wherein the haloalkyl solvent comprises dichloromethane, chloroform, or dichloroethane, or any combinations thereof.

64. The method of any one of embodiments 31 to 63, wherein less than 50% of the halomethyl group of the halomethylfurfural is hydrolyzed to a hydroxymethyl group.

65. The method of any of embodiments 31 to 64, wherein the halomethylfuroic acid, or a salt thereof, is a solid.

66. The method of any one of embodiments 1 to 7 or 10 to 30, wherein the salt of the compound of formula (II) is a compound of formula (IIX-Ai):

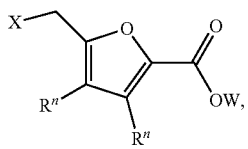

(IIX-Ai)

wherein:
each $R^n$ is independently H or alkyl;
X is halo; and
W is a cation.

67. The method of embodiment 66, wherein the compound of formula (IIX) is produced at a yield of at least 50%.

68. The method of embodiment 1, wherein the compound of formula (I) is a compound of formula (I-Bi), and the compound of formula (II) is a compound of formula (II-Bi), or a salt thereof, wherein:
the compound of formula (I-Bi) is:

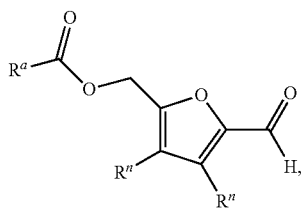

(I-Bi)

wherein each $R^n$ is independently H or alkyl; and
$R^a$ is H, aliphatic or aromatic;
the compound of formula (II-Bi) is:

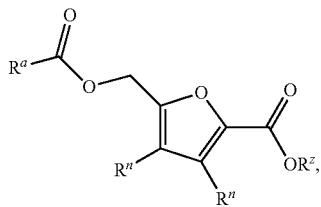

(II-Bi)

wherein $R^n$ and $R^a$ are as defined for formula (I-Bi); and
$R^z$ is H.

69. The method of embodiment 68, wherein the salt of the compound of formula (II-Bi) is a compound of formula (IIX-Bi):

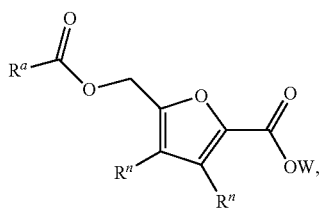

(IIX-Ci)

wherein:
W and $R^a$ are as defined for formula (I-Bi); and
W is a cation.

70. The method of any one of embodiments 66, 67 or 69, wherein W is $Na^+$, $Li^+$, or $K^+$.

71. The method of any one of embodiments 66, 67 or 69, wherein the oxidant is a compound of formula $W^b$-$O_2X^b$, and $W^b$ and W are the same Group I cation.

72. The method of any one of embodiments 66 to 71, wherein the compound of formula (I) and the oxidant are combined in the presence of water.

73. The method of any one of embodiments 66 to 72, wherein each $R^n$ is H.

74. The method of any one of embodiments 66 to 72, wherein each $R^n$ is independently alkyl.

75. The method of any one of embodiments 66 to 72, wherein one $R^n$ is alkyl and the other $R^n$ is H.

76. The method of any one of embodiments 68 to 75, wherein $R^a$ is n-undecyl.

77. The method of any one of embodiments 66 to 76, wherein the combining of the compound of formula (I) and the oxidant forms a reaction mixture.

78. The method of embodiment 77, wherein the reaction mixture further comprises water.

79. The method of embodiment 78, wherein the reaction mixture is biphasic.

80. The method of any one of embodiments 77 to 79, wherein the reaction mixture further comprises a phase transfer catalyst.

81. The method of any one of embodiments 68 to 72, or 77 to 80, wherein the compound of formula (II) is:

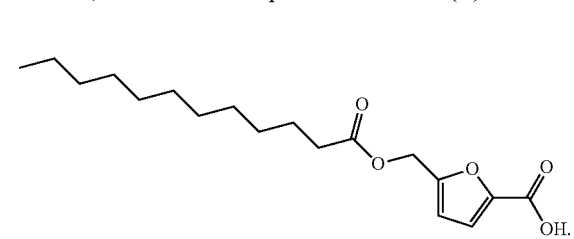

82. The method of any one of embodiments 66 to 81, wherein the oxidant is a compound of formula $W^b$-$O_2X^b$.

83. The method of embodiment 82, wherein $W^b$ is a $Na^r$, and $X^b$ is chloro.

84. A method of producing a halomethylfuroic ester comprising combining a halomethylfurfural, an alcohol, and an oxidant to produce a halomethylfuroic ester,
wherein the oxidant is:
(i) a compound of formula $W^b$-$O_2X^b$, wherein $W^b$ is a Group I cation and $X^b$ is halo;
(ii) $W^d$-$O_3X^d$, wherein $W^d$ is a Group I cation and $X^d$ is halo;
(iii) $HX^bO_2$, wherein $X^b$ is halo;
(iv) $HX^dO_3$, wherein $X^d$ is halo; or
(v) $X^cO_2$, wherein $X^c$ is halo.

85. A method of producing a compound of formula (II-Bi), comprising combining a compound of formula (I-Bi) with an alcohol and an oxidant to produce the compound of formula (II-Bi) wherein:
the compound of formula (I-Bi) is:

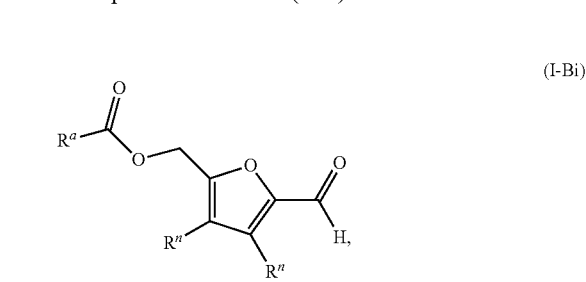

(I-Bi)

wherein each $R^n$ is independently H or alkyl; and
$R^a$ is H, aliphatic or aromatic;

the compound of formula (II-B) is:

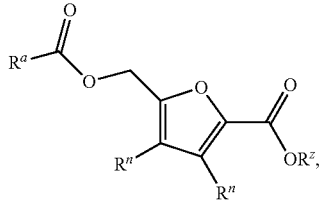

wherein W and $R^a$ are as defined for formula (I-Bi); and
$R^z$ is aliphatic; and
the oxidant is:
(i) a compound of formula $W^a$-$X^bO_2$,
(ii) a compound of formula $HX^bO_2$, or
(iii) a compound of formula $X^bO_2$,
wherein $W^a$ is a Group I cation and $X^b$ is independently halo.

86. A compound of formula (II-Bi), or a salt thereof:

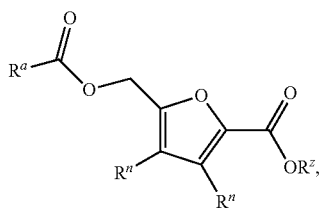

wherein:
each $R^n$ is independently H or alkyl;
$R^a$ is H, aliphatic or aromatic; and
$R^z$ is H or aliphatic.

87. The compound of embodiment 86, wherein the salt of the compound of formula (II-Bi) is a compound of formula (IIX-Bi):

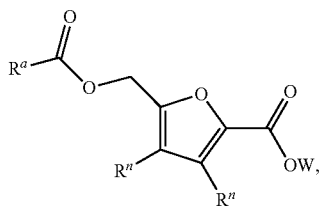

wherein:
$R^n$ and $R^a$ are as defined for formula (I-Bi); and
W is a cation.

88. The compound of embodiment 86, wherein the compound of formula (II-Bi) is:

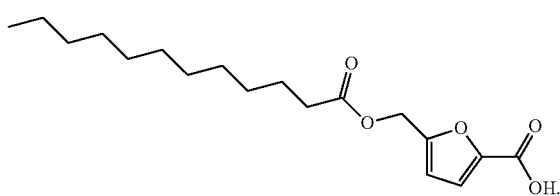 [SMILES: CCCCCCCCCCCC(=O)OCc1ccc(C(=O)O)o1]

89. The compound of embodiment 87, wherein compound of formula (IIX-Bi) is:

wherein W is a cation.

EXAMPLES

The following Examples are merely illustrative and are not meant to limit any aspects of the present disclosure in any way.

Example 1

Reaction of 5-chloromethylfurfural with $NaClO_2$ at Varying pH

This Example demonstrates the difference in reaction progression observed in the oxidation of 5-chloromethylfurfural (CMF) by $NaClO_2$ at different pH.

In 60 mL of acetonitrile was dissolved 1.5 g (0.0104 mol) of 5-chloromethylfurfural (CMF). In a separate flask, a solution of 4.62 g (0.0414 mol) of sodium chlorite (81% assay) was prepared in 60 mL of deionized (DI) water. The aqueous solution was equally divided into six 25 mL Erlenmeyer flasks. To each flask was added 1 mL of pH 6.5 sodium phosphate buffer solution. The pH of the $NaClO_2$ solution with buffer was greater than 10. The pH in each flask was then adjusted using either 0.5 M NaOH or 1 M HCl, to achieve a pH of 1.5, 2.5, 4.0, 5.5, 7.0, or 8.5. The solution in the two lowest pH flasks (1.5 and 2.5) was bright yellow.

To each flask was then added 10 mL of the CMF dissolved in acetonitrile. The flasks were swirled for a few seconds to mix the two phases, resulting in homogeneous solutions in all the flasks. The flasks were left to stand undisturbed for 30 min. Some bubbles of gas collected on the walls of all the flasks with initial pH<7. After 30 min, samples were taken using thin layer chromatography (TLC) capillaries (1 microliter) and spotted on TLC plates. Development of the plates with 1:1 ether/hexanes (UV visualization) showed that CMF was the only component in the flasks with starting pH of 4.0 and above. In the flasks starting at 1.5 and 2.5, a new spot was visible with an $R_f$ of 0.147. This did not correspond with the $R_f$ of any of the compounds for which standards were available. (CMF=0.352, 5-hydroxymethylfurfural (HMF)= 0.099, 5-hydroxymethyl-2-furoic acid (HMFA)=0.035, 5-formyl-2-furoic acid (FFA) about 0.035).

The six flasks were allowed to stand for a total of 16.75 and then rechecked by TLC. The solution in the flask starting at pH 1.5 was colorless. The other five solutions were similar shades of yellow. The color developed faster in the more acidic solutions. TLCs of the solutions showed that all of them still had some CMF remaining and a significant spot was visible at the origin (likely inorganic salts), with some streaking, suggesting that some HMFA had been produced. There was no spot corresponding to an $R_f$ of 0.147, but a dark spot with an $R_f$ corresponding to HMF was visible for each of the solutions.

The solutions were allowed to stand a further 24 h at room temperature and checked again by TLC. No further changes were observed in the TLCs of the reaction mixtures. The solution that had originally been at pH 2.5 had also become colorless. The pH of all six solutions was measured. All had become more acidic. The solutions which started at pH 1.5, 2.5, 4.0, 5.5, 7.0, and 8.5 had measured values of 0.80, 1.76, 2.44, 2.52, 3.36, and 3.17, respectfully.

Thus, this experiment demonstrated that the observed reaction of CMF with $NaOCl_2$ proceeds differently at different pH.

Example 2

Reaction of CMF with $NaClO_2$ and Product Mixture Analysis

This Example demonstrates the reaction of 5-chloromethylfurfural with $NaClO_2$ and analysis of the product mixture by TCL, gas chromatography (GC), NMR, and yield calculation.

A solution of CMF (2.0 g, 0.014 mol) in 50 mL of acetonitrile and 4.8 g (0.0616 mol) of dimethyl sulfoxide was placed in an addition funnel. To a 250 mL round bottom flask cooled in an ice water bath was added a solution of 3.50 g of 81% sodium chlorite (0.0314 mol) in 50 mL of deionized water. To this was added 3.04 g of 37% hydrochloric acid (0.0308 mol), maintaining the mixture between 4° C. and 8° C. The CMF solution in the addition funnel was added drop-wise to the acidic sodium chlorite solution in the round bottom flask over approximately 70 min. The reaction was monitored by TLC (silica gel, 15% $CH_3OH$/85% $CHCl_3$/0.1% $HCO_2H$, UV visualization) during the addition, and showed little or no CMF in the reaction mixture until the end of the addition. Without wishing to be bound by any theory, this suggested the reaction occurs very quickly, such as a titration. A sample of the mixture was taken after the addition was complete and NMR spectra ($^{13}C—$, $^1H—$, $^{13}C$-DEPT135) were acquired. The $^{13}C$-NMR acquisition was performed over 12 h. $^1H$-NMR peak assignments for 5-chloromethyl-2-furoic acid (CMFA) ($CDCl_3$, 300 MHz): δ 10.90 (broad singlet, 1H), 7.22 (doublet (J=3.49 Hz), 1H), 6.53 (doublet (J=3.49 Hz), 1H), 4.615 (singlet, 2H). $^{13}C$-NMR peak assignments for CMFA ($CDCl_3$, 75 MHz): δ 161.6, 154.76, 144.6, 119.99, 111.63, 36.66. The reaction appeared to have given a good yield of 5-chloromethyl-2-furoic acid. Analysis of the reaction mixture by TLC the next morning showed a spot for 5-chloromethyl-2-furoic acid, and a faint spot for 5-hydroxymethylfuroic acid. A trace of CMF was visible.

Isolation of the 5-chloromethyl-2-furoic acid: The reaction mixture was poured into a 250 mL separatory funnel and extracted 3 times with 30-35 mL of $CH_2Cl_2$ each extraction. The combined organic phase extracts were washed once with 20 mL of 49 wt % $CaCl_2$ solution in water. The total volume of aqueous phase remaining was about 75 mL. The organic phase was dried with 3-5 g of $MgSO_4$ and filtered to remove insoluble matter using #2 Whatman® paper in a Buchner funnel. The solids were washed with about 10 mL of $CH_2Cl_2$. The aqueous phase and organic phase were analyzed by TLC. The organic phase contained mostly 5-chloromethyl-2-furoic acid and a trace of 5-hydroxymethyl-2-furoic acid. The aqueous phase had a noticeable spot corresponding to 5-hydroxymethyl-2-furoic acid but no other spots that moved from the origin. The acetonitrile and methylene chloride were removed by evaporation overnight in a hood under a stream of dry nitrogen.

The residue remaining in the flask after evaporation was a white to pale yellow solid weighing 3.33 g. $^{13}C—$ and $^1H$-NMR spectra were acquired on a 50 mg sample in $CDCl_3$. The $^{13}C$-NMR was nearly identical to the spectrum taken of the reaction mixture, except for the absence of $CH_3CN$ and the lower level of dimethyl sulfoxide. The $^1H$-NMR showed the carboxylic acid proton at 11 ppm with integrated areas for all the peaks for 5-chloromethyl-2-furoic acid, along with a significant amount of dimethylsulfone. A portion of the NMR sample was diluted with $CH_2Cl_2$ and analyzed by gas chromatography (GC). The acid came out at about 13.5 min. The NMR sample was analyzed by TLC, which showed that the materials before and after isolation had the same $R_f$, further suggesting that the immediate product of the oxidation of CMF with $NaClO_2$ under strongly acid conditions is 5-chloromethyl-2-furoic acid. The relative integrated areas for the dimethylsulfone peak and the chloromethylene peak give a mole ratio of dimethylsulfone to 5-chloromethyl-2-furoic acid of ~1.275:1. Converting this to wt %, the purity of the acid is about 57%. After correcting for the residual DMSO in the sample, the isolated yield of 5-chloromethyl-2-furoic acid is 83.6%. The reaction analysis for this Example is shown in Table 1. The product analysis is shown in Table 2.

TABLE 1

Reaction analysis.

| | Components of Mixture | | | | | | |
|---|---|---|---|---|---|---|---|
| | $CH_3CN$ | DMSO | sulfone | CMFA | CMF | $CH_2Cl_2$ | Total moles |
| Grams | 39.30 | 4.80 | 0 | 0 | 2.00 | | |
| MW | 96.10 | 78.13 | 94.13 | 160.56 | 144.56 | 84.93 | |
| Moles | 0.4089 | 0.0614 | 0.0000 | 0.0000 | 0.0138 | | 0.4704 |

TABLE 2

Product analysis.

| Products ($^1H$-NMR peak assignments) | Area | Molar Response | Proportional Weight | wt % | Sample Weight | % yield |
|---|---|---|---|---|---|---|
| CMFA (4.6 ppm) | 20.000 | 10.000 | 1.606 | 55.79 | 1.858 | 83.6 |
| acetonitrile (2.0 ppm) | 0.000 | 0.000 | 0.000 | 0.00 | 0.000 | |
| dimethylsulfoxide (2.8 ppm) | 5.489 | 0.915 | 0.071 | 2.48 | 0.083 | 1.7 |
| dimethylsulfone (3.0 ppm) | 76.539 | 12.757 | 1.201 | 41.72 | 1.389 | 24.0 |
| Sum | | 23.671 | 2.878 | | | |

Example 3

Reaction of 5-chloromethylfurfural with NaClO₂ at Low pH

This Example demonstrates reaction progression observed in the oxidation of 5-chloromethylfurfural (CMF) by $NaClO_2$ at low pH.

A solution of CMF (2.0 g, 0.014 mol) in 50 mL of acetonitrile and 4.8 g (0.0616 mol) of dimethyl sulfoxide was placed in an addition funnel. To a 250 mL round bottom flask was added 3.51 g of 81% sodium chlorite (0.0314 mol). Deionized water (50 mL) was added and the slurry was stirred until the solid dissolved. The solution was cooled in an ice water bath to <5° C. To this was added 3.04 g of 37% hydrochloric acid (0.0308 mol), maintaining the mixture between 4 and 8° C. The CMF solution was added drop-wise to the acidic sodium chlorite solution. The addition took about 44 min. The reaction was analyzed by TLC about 1 h after starting the CMF addition, and showed clean conversion of the CMF to CMFA (5-chloromethylfuroic acid). The ice bath was removed about 10 minutes later and the mixture was allowed to warm to room temperature. The reaction was analyzed by TLC again about 1 h later, and showed nearly complete conversion of the CMF; only a very faint spot for CMF was observed. The reaction was analyzed a third time by TLC another hour later, and again the CMF spot was very faint. The reaction mixture was placed in the refrigerator overnight (<5° C.).

Analysis of the reaction mixture by TLC the next morning showed a spot for CMFA, and a faint one for the 5-hydroxymethylfuroic acid. The mixture was stirred and 1.01 g (8 mmol) of $Na_2SO_3$ was added. Stirring continued until the solid dissolved. A small upper phase (slightly darker color than the bottom phase) was observed in the flask. The reaction mixture was poured into a separatory funnel along with 25 mL of $CH_2Cl_2$. The mixture was shaken, allowed to settle, and then the bottom phase was drained and collected. When a second 25 mL portion of $CH_2Cl_2$ was added, phase inversion occurred. Everything was put back in the separatory funnel and the bottom (organic) phase was drained off. The remaining aqueous phase was extracted a third time with $CH_2Cl_2$. The combined organic phase was dried with 3 to 5 g of $MgSO_4$ and filtered to remove insoluble matter using #2 Whatman® paper in a Buchner funnel. The solids were washed with about 10 mL of $CH_2Cl_2$. The colorless aqueous phase and yellow organic phase were analyzed by TLC. The organic phase contained mostly 5-chloromethyl-2-furoic acid and trace 5-hydroxymethylfuroic acid. The aqueous phase had a noticeable spot corresponding to 5-hydroxymethyl-2-furoic acid, but nothing else moved from the origin.

The acetonitrile and methylene chloride were removed by evaporation overnight in a hood under a stream of dry nitrogen. The residue remaining in the flask after evaporation was a pale yellow semi-solid weighing 4.26 g. $^{13}C$— and $^1H$-NMR spectra were acquired on a 134.1 mg sample in $CDCl_3$. $^1H$-NMR peak assignments for CMFA ($CDCl_3$, 300 MHz): δ 10.90 (broad singlet, 1H), 7.22 (doublet (J=3.49 hz), 1H), 6.53 (doublet (J=3.49 hz), 1H), 4.615 (singlet, 2H). $^{13}C$-NMR peak assignments for CMFA ($CDCl_3$, 75 MHz): δ 161.6, 154.76, 144.6, 119.99, 111.63, 36.66. The $^{13}C$-NMR showed $CH_3CN$, dimethyl sulfoxide, and dimethylsulfone in addition to CMFA. The $^1H$-NMR clearly showed the carboxylic acid proton at 10 ppm with integrated areas for all the peaks corresponding to 5-chloromethyl-2-furoic acid.

TABLE 3

Reaction analysis.

| | Components of Mixture | | | | | Total |
|---|---|---|---|---|---|---|
| | CH₃CN | DMSO | sulfone | CMFA | CMF | moles |
| Grams | 39.30 | 4.80 | 0 | 0 | 2.00 | |
| MW | 96.10 | 78.13 | 94.13 | 160.56 | 144.56 | |
| Moles | 0.4089 | 0.0614 | 0.0000 | 0.0000 | 0.0138 | 0.4704 |

TABLE 4

Product analysis.

| Products (¹H-NMR peak assignments) | Area | Molar Response | Proportional Weight | wt % | Sample Weight | % yield |
|---|---|---|---|---|---|---|
| CMFA (4.6 ppm) | 20.000 | 10.000 | 1.606 | 38.72 | 1.650 | 74.3 |
| acetonitrile (2.0 ppm) | 20.062 | 6.687 | 0.643 | 15.50 | 0.660 | |
| dimethylsulfoxide (2.8 ppm) | 34.362 | 5.727 | 0.447 | 10.79 | 0.460 | 9.6 |
| dimethylsulfone (3.0 ppm) | 92.481 | 15.414 | 1.451 | 34.99 | 1.491 | 25.8 |
| Sum | | 37.828 | 4.147 | | | |

Example 4

Effect of Reactant Mole Ratio on Yield

This Example demonstrates the effect that the mole ratio of oxidant to reactant has on the oxidation of CMF to CMFA by $NaClO_2$.

A solution of CMF (5-chloromethylfurfural) (2.00 g, 0.0138 mol) in 50 mL of acetonitrile and 4.8 g (0.0616 mol) of dimethyl sulfoxide was placed in an addition funnel. To a 250 mL round bottom flask was added 2.70 g of 81% sodium chlorite (0.0242 mol). Deionized water (50 mL) was added and the slurry was stirred until the solid dissolved. The solution was cooled in an ice water bath to <5° C. To this was added 2.38 g of 37% hydrochloric acid (0.0242 mol), maintaining the mixture between 4 and 8° C. The CMF solution was added drop-wise to the acidic sodium chlorite solution. The addition took about 44 min. A TLC (silica gel, developed in 15% $CH_3OH$/85% $CHCl_3$/0.1% $HCO_2H$, UV visualization) of the reaction about 1 h after starting the CMF addition showed very clean conversion of the CMF to CMFA (5-chloromethyl-2-furoic acid). The ice bath was removed. The reaction mixture was placed in the refrigerator overnight (<5° C.).

Analysis of the reaction mixture by TLC the next morning showed a spot for the CMFA, and a faint spot for 5-hydroxymethylfuroic acid. The mixture was stirred and 3.44 g (27.3 mmol) of $Na_2SO_3$ was added. Stirring continued until the solid dissolved. This amount of sodium sulfite was sufficient to discharge the yellow color originally visible throughout the reaction mixture. The reaction mixture was poured into a 250 mL separatory funnel along with 25 mL of $CH_2Cl_2$. The mixture was shaken, allowed to settle, and then the bottom (aqueous) phase was drained off. The $CH_2Cl_2/CH_3CN$ phase was drained to a 250 mL Erlenmeyer flask. When a second 25 mL portion of $CH_2Cl_2$ was added to the aqueous phase which was returned to the separatory funnel, phase inversion occurred. This time the $CH_2Cl_2$ phase was on the bottom. After shaking, the bottom (organic) phase was drained off into the 250 mL Erlenmeyer flask. The remaining aqueous phase was extracted a third time with CH$_2$Cl$_2$. The combined organic phase was dried with 3 to 5 g of MgSO$_4$ and filtered to remove insoluble matter using a coarse sintered glass frit funnel. The solids were washed with about 10 mL of CH$_2$Cl$_2$. The colorless organic phase was analyzed by TLC. The organic phase contained mostly 5-chloromethyl-2-furoic acid and a trace of 5-hydroxymethylfuroic acid.

The organic solution was concentrated on the rotary evaporator, bath temperature 40° C. The partially solid, pale yellow residue weighed 4.24 g. This was re-dissolved in 25 mL of fresh CH$_2$Cl$_2$ and transferred into a 125 mL separatory funnel. The organics were washed with 20 mL of 1:1 saturated NaCl brine/DI water. The CH$_2$Cl$_2$ solution was concentrated to dryness again on the rotary evaporator (bath temperature 30° C.). Some bumping occurred, so the solids were rinsed down with a minimal amount of CH$_2$Cl$_2$ and carefully concentrated to give a pale yellow, sticky solid, weight 3.31 g. A 72 mg sample was dissolved in CDCl$_3$/TMS and analyzed by $^1$H— and $^{13}$C-NMR. $^1$H-NMR peak assignments for CMFA (CDCl$_3$, 300 MHz): δ 10.90 (broad singlet, 1H), 7.22 (doublet (J=3.49 Hz), 1H), 6.53 (doublet (J=3.49 Hz), 1H), 4.615 (singlet, 2H). $^{13}$C-NMR peak assignments for CMFA (CDCl$_3$, 75 MHz): δ 161.6, 154.76, 144.6, 119.99, 111.63, 36.66. The material was 62.3 wt % CMFA, which is a 92.8% yield, higher than when a larger excess of NaClO$_2$ was employed for the oxidation as described in Example 2 above. The reaction analysis is shown in Table 3. The product analysis is shown in Table 4.

TABLE 3

Reaction analysis.

| | Components of Mixture | | | | | |
|---|---|---|---|---|---|---|
| | CH$_3$CN | DMSO | sulfone | CMFA | CMF | CH$_2$Cl$_2$ | Total moles |
| Grams | 39.30 | 4.80 | 0 | 0 | 2.00 | | |
| MW | 96.10 | 78.13 | 94.13 | 160.56 | 144.56 | 84.93 | |
| Moles | 0.4089 | 0.0614 | 0.0000 | 0.0000 | 0.0138 | | 0.4704 |

TABLE 4

Product analysis.

| Products ($^1$H-NMR peak assignments) | Area | Molar Response | Proportional Weight | wt % | Sample Weight | % yield |
|---|---|---|---|---|---|---|
| CMFA (4.6 ppm) | 20.000 | 10.000 | 1.606 | 62.29 | 2.062 | 92.8 |
| acetonitrile (2.0 ppm) | 0.000 | 0.000 | 0.000 | 0.00 | 0.000 | |
| dimethylsulfoxide (2.8 ppm) | 22.772 | 3.795 | 0.297 | 11.50 | 0.381 | 7.9 |
| dimethylsulfone (3.0 ppm) | 39.929 | 6.655 | 0.626 | 24.30 | 0.804 | 13.9 |
| methylene chloride (53 ppm) | 1.159 | 0.580 | 0.049 | 1.91 | 0.063 | |
| Sum | | 21.030 | 2.578 | | | |

Example 5

Effect of Water Concentration on Oxidation of CMF to CMFA

This Example demonstrates how different amounts of water in the reaction mixture affect the oxidation of CMF and the level of byproducts obtained.

Two separate reactions were performed concurrently, one with a higher ratio of water to organic solvent, and one with a lower ratio of water to organic solvent.

Reaction set up with higher water concentration (A): A solution of CMF (5-chloromethylfurfural) (4.0 g, 0.0277 mol) in 50 mL of acetonitrile and 9.6 g (0.123 mol) of dimethyl sulfoxide was placed in an addition funnel. To a 250 mL round bottom flask was added 5.40 g of 81% sodium chlorite (0.0484 mol). Deionized water (100 mL) was added and the slurry was stirred until the solid dissolved. The solution was cooled in an ice water bath to <5° C. To this was added 4.76 g of 37% hydrochloric acid (0.0483 mol), pre-chilled in ice water, maintaining the mixture between 4 and 8° C. The CMF solution was added drop-wise to the acidic sodium chlorite solution. The addition took about 1 hour. The temperature was mostly kept below 8° C., but did reach about 18° C. for a brief period. A solid precipitate was observed early on in the addition. The solution became homogeneous after about two-thirds of the CMF solution had been added.

Reaction set up with lower water concentration (B): A solution of CMF (5-chloromethylfurfural) (4.00 g, 0.0277 mol) in 100 mL of acetonitrile and 9.6 g (0.123 mol) of dimethyl sulfoxide was placed in an addition funnel. To a 250 mL round bottom flask was added 5.40 g of 81% sodium chlorite (0.0484 mol). Deionized water (50 mL) was added and the slurry was stirred until the solid dissolved. The solution was cooled in an ice water bath to <5° C. To this was added 4.76 g of 37% hydrochloric acid (0.0483 mol), pre-chilled in ice water, maintaining the NaClO$_2$ solution between 4 and 8° C. The CMF solution was added drop-wise to the acidic sodium chlorite solution. The addition took about 1 hour. The reaction mixture took on a cloudy appearance and two separate liquid phases were observed. The reaction appeared to be darker yellow than the reaction run with a higher volume of water.

Observations of both reactions: Both reactions were analyzed by TLC about 30 minutes after finishing the CMF addition (silica gel, developed in 15% CH$_3$OH/85% CHCl$_3$/0.1% HCO$_2$H, UV visualization). Both reactions showed significant conversion of the CMF to CMFA (5-chloromethyl-2-furoic acid). The ice bath was left in place around the flasks and the mixtures were allowed to stir and warm to room temperature overnight.

The reaction mixtures were analyzed by TLC the next morning. The reaction with a higher water concentration (A) had a spot for CMFA, and a dark spot for 5-hydroxymethylfuroic acid, while the reaction with a lower water concentration (B) had a spot for the CMFA, a faint spot for 5-hydroxymethylfuroic acid, and a spot for unreacted CMF. The reaction mixture with more water was lighter in color than that with less water, which was a dark yellow.

The mixtures were stirred and cooled to <5° C. in an ice water bath. Solid $Na_2SO_3$, 2.0 g (0.0159 mol) was added in small portions, with continued stirring until the solid dissolved. This amount of sulfite was sufficient to discharge the yellow color observed throughout the reaction mixtures. Each reaction mixture was poured into a separatory funnel along with 35 mL of $CH_2Cl_2$.

For each reaction, the mixture was shaken, allowed to settle, and the organic phase removed. The remaining aqueous phase was extracted twice more with $CH_2Cl_2$. For each separate reaction, the combined organic phase and the aqueous phase were analyzed by TLC.

The organic phase of reaction (A) contained mostly 5-chloromethyl-2-furoic acid and a trace of 5-hydroxymethylfuroic acid. The aqueous phase had a noticeable spot corresponding to 5-hydroxymethyl-2-furoic acid and an unknown spot that moved slightly from the origin. The organic phase of reaction (B) mostly 5-chloromethyl-2-furoic acid, CMF, and a trace of 5-hydroxymethylfuroic acid. The aqueous phase had a noticeable spot corresponding to 5-hydroxymethyl-2-furoic acid and an unknown spot that moved slightly from the origin.

For both reactions, the acetonitrile and methylene chloride were removed by evaporation on the rotary evaporator with a bath temperature of 30 to 35° C. The pale yellow semi-solid residue (reaction (A): 7.09 g; reaction (B): 12.94 g) was re-dissolved in 25 mL of $CH_2Cl_2$ and poured into a 125 mL separatory funnel. A 1:1 mixture of 10 mL of saturated NaCl brine and 10 mL of DI water was used to wash the CMFA solution in $CH_2Cl_2$ to remove some of the residual DMSO. The $CH_2Cl_2$ solution was then re-concentrated to dryness on the rotary evaporator and then stored under a nitrogen purge for at least 48 hours.

Analysis of reaction (A): The residue remaining in the flask after evaporation was a pale yellow semi-solid weighing 4.22 g. $^{13}$C— and $^1$H-NMR spectra were acquired on a 65 mg sample in $CDCl_3$. $^1$H-NMR peak assignments for CMFA ($CDCl_3$, 300 MHz): δ 10.90 (broad singlet, 1H), 7.22 (doublet (J=3.49 Hz), 1H), 6.53 (doublet (J=3.49 Hz), 1H), 4.615 (singlet, 2H). $^{13}$C-NMR peak assignments for CMFA ($CDCl_3$, 75 MHz): δ 161.6, 154.76, 144.6, 119.99, 111.63, 36.66. The $^{13}$C-NMR showed dimethyl sulfoxide, dimethylsulfone, and CMFA. The $^1$H-NMR showed the broad carboxylic acid proton resonance at 9.5 ppm with integrated areas for all the peaks consistent with 5-chloromethyl-2-furoic acid. The intense spot for 5-hydroxymethylfuroic acid in the crude reaction mixture and aqueous phase suggests that a major reason for the relatively modest yield of CMFA was due to hydrolysis in the aqueous environment before workup. Little or no CMF was visible in this reaction either by TLC or NMR analysis. The analysis of reaction (A) is shown in Table 5. The analysis of product from reaction (A) is shown in Table 6.

Analysis of reaction (B): The residue remaining in the flask after evaporation was a pale yellow semi-solid weighing 6.58 g. $^{13}$C— and $^1$H-NMR spectra were acquired on a 65 mg sample in $CDCl_3$. $^1$H-NMR peak assignments for CMFA ($CDCl_3$, 300 MHz): δ 10.90 (broad singlet, 1H), 7.22 (doublet (J=3.49 Hz), 1H), 6.53 (doublet (J=3.49 Hz), 1H), 4.615 (singlet, 2H). $^{13}$C-NMR peak assignments for CMFA ($CDCl_3$, 75 MHz): δ 161.6, 154.76, 144.6, 119.99, 111.63, 36.66. The $^{13}$C-NMR showed dimethyl sulfoxide, dimethylsulfone, and unreacted CMF in addition to CMFA. The $^1$H-NMR showed the broad carboxylic acid proton resonance at 10.3 ppm and a resonance for the aldehyde proton of CMF at 9.6 ppm. The peak areas in the $^1$H-NMR analysis were used to calculate that about 19% of the original CMF was present in the crude product. The integrated areas for all the peaks corresponded to 5-chloromethyl-2-furoic acid, after taking into account the areas of the overlapping resonances for CMF. The analysis of reaction (B) is shown in Table 7. The analysis of product from reaction (B) is shown in Table 8.

For both reactions, the approximate yield of CMFA was about the same. The oxidation was more efficient in the system containing the most water, based on the amount of 5-hydroxymethylfuroic acid present, which is the product of CMFA hydrolysis.

TABLE 5

Analysis of reaction (A).

| | Components of Mixture | | | | | | |
|---|---|---|---|---|---|---|---|
| | $CH_3CN$ | DMSO | sulfone | CMFA | CMF | $CH_2Cl_2$ | Total Moles |
| Grams | 39.30 | 9.60 | 0 | 0 | 4.00 | | |
| MW | 96.10 | 78.13 | 94.13 | 160.56 | 144.56 | 84.93 | |
| Moles | 0.4089 | 0.1229 | 0.0000 | 0.0000 | 0.0277 | | 0.5318 |

TABLE 6

Analysis of product from reaction (A).

| Products ($^1$H-NMR peak assignments) | Area | Molar Response | Proportional Weight | wt % | Sample Weight | % yield |
|---|---|---|---|---|---|---|
| CMFA (4.6 ppm) | 20.000 | 10.000 | 1.606 | 55.80 | 2.355 | 53.0 |
| acetonitrile (2.0 ppm) | 0.000 | 0.000 | 0.000 | 0.00 | 0.000 | |
| dimethyl sulfoxide (2.8 ppm) | 14.827 | 2.471 | 0.193 | 6.71 | 0.283 | 2.9 |
| dimethylsulfone (3.0 ppm) | 68.771 | 11.462 | 1.079 | 37.49 | 1.582 | 13.7 |
| methylene chloride (5.3 ppm) | 0.000 | 0.000 | 0.000 | 0.00 | 0.000 | |
| Sums | | 23.933 | 2.878 | | | |

TABLE 7

Analysis of reaction (B).

| | Components of Mixture | | | | | |
|---|---|---|---|---|---|---|
| | $CH_3CN$ | DMSO | sulfone | CMFA | CMF | $CH_2Cl_2$ | Total Moles |
| Grams | 78.60 | 9.60 | 0 | 0 | 4.00 | | |
| MW | 96.10 | 78.13 | 94.13 | 160.56 | 144.56 | 84.93 | |
| Moles | 0.8179 | 0.1229 | 0.0000 | 0.0000 | 0.0277 | | 0.9408 |

TABLE 8

Analysis of reaction (B).

| Products ($^1$H-NMR peak assignments) | Area | Molar Response | Proportional Weight | wt % | Sample Weight | % yield |
|---|---|---|---|---|---|---|
| CMFA (4.6 ppm) | 17.680 | 8.840 | 1.419 | 37.12 | 2.442 | 55.0 |
| acetonitrile (2.0 ppm) | 0.000 | 0.000 | 0.000 | 0.00 | 0.000 | |
| dimethyl sulfoxide (2.8 ppm) | 21.354 | 3.559 | 0.278 | 7.27 | 0.479 | 5.0 |
| dimethylsulfone (3.0 ppm) | 107.243 | 17.874 | 1.682 | 44.00 | 2.895 | 25.0 |
| CMF (6.6 ppm) | 3.070 | 3.070 | 0.444 | 11.61 | 0.764 | 19.1 |
| methylene chloride (5.3 ppm) | 0.000 | 0.000 | 0.000 | 0.00 | 0.000 | |
| Sums | | 33.343 | 3.824 | | | |

Example 6

Oxidation of a Hydroxymethylfurfural Ester

This Example demonstrates the oxidation of an ester of hydroxymethyl furfural to produce the corresponding acid.

A sample of the dodecanoate ester of 5-hydroxymethyl-furfural ((5-formylfuran-2-yl)methyl dodecanoate) (1.00 g, 3.24 mmol) was slurried in 50 mL of acetonitrile and 1.01 g (0.0130 mol) of dimethylsulfoxide (4 equiv.). The mixture was stirred until most of the solid dissolved. Meanwhile, to a 250 mL round bottom flask was added 0.63 g of 81% sodium chlorite (5.67 mmol) (1.75 equiv.). Deionized water (50 mL) was added and the slurry was stirred until the solid dissolved. The solution was cooled in an ice water bath to <5° C. To this was added 0.56 g of chilled 37% hydrochloric acid (5.67 mmol) in one portion, using a pipet. The acetonitrile containing the ester was cooled in an ice water bath and then poured in one portion into the acidic sodium chlorite solution. Momentarily, the mixture stirred, and then a white solid precipitated out of solution and all stirring stopped. The reaction was not observed to be exothermic (mixture stayed at about 5° C.). The reaction was analyzed by TLC (silica gel, 50/50 Et$_2$O/hexanes, UV visualization) about 1 h after mixing the reagents, and showed only a slower moving spot on the plate. It is likely that a representative sample was not obtained for TLC analysis due to the heterogeneous nature of the reaction mixture. About 2 h after mixing the reagents, 25 mL of 1,2-dimethoxyethane was added, thinning the slurry, and the mixture resumed slow stirring. The mixture warmed to the range of 15-20° C. The ice bath was allowed to melt while stirring continued overnight.

Analysis of the reaction mixture by TLC the next morning showed only one spot, attributed to the dodecanoate ester of 5-hydroxymethylfuroic acid (5-((dodecanoyloxy)methyl)furan-2-carboxylic acid). The mixture was stirred and 1.42 g (11.3 mmol) of Na$_2$SO$_3$ was added. Stirring continued until the solid dissolved. This amount of sodium sulfite was sufficient to discharge the yellow color originally visible throughout the reaction mixture. The reaction mixture was poured into a 250 mL separatory funnel along with 25 mL of chloroform. The mixture was shaken and allowed to settle. Two liquid phases were present, along with a suspended white solid. The entire mixture was filtered through a thin layer of Celite® 521 filter aid. The filter cake was washed with two 5 mL portions of additional chloroform. The filtrate was returned to a clean 250 mL separatory funnel and the bottom (chloroform/acetonitrile/1,2-dimethoxyethane) phase was drained into a 250 mL round bottom flask. The aqueous phase was shaken a second time with 25 mL of chloroform and the chloroform extract was added to the previous collected organic phase. The combined organic phases were concentrated to a solid using the rotary evaporator. The weight of material isolated was 1.11 g. About 30 mg was dissolved in 0.7 mL of CDCl$_3$ giving a clear, nearly colorless solution, and $^1$H— and $^{13}$C-NMR spectra were obtained. $^1$H-NMR peak assignments for the acid product (CDCl$_3$, 300 MHz): δ 8.90 (broad singlet, 1H), 7.21 (doublet (J=3.395 hz), 1H), 6.52 (doublet (J=3.395 hz), 1H), 5.106 (singlet, 2H), 2.34 (triplet (J=7.66 hz), 2H), 1.62 (broad triplet (J=7.16 hz), 2H), 1.25 (broad singlet, 16H), 0.88 (triplet (J=6.68 hz), 3H). $^{13}$C-NMR peak assignments for the acid product (CDCl$_3$, 75 MHz): δ 173.28, 161.77, 154.25, 144.59, 119.74, 112.20, 57.68, 33.99, 31.86, 29.54, 29.39, 29.28, 29.17, 29.04, 24.78, 22.63, 14.06. These confirmed that the material was mostly the corresponding furoic acid. Some DMSO was observed, along with a byproduct, dimethyl sulfone. An approximate analysis by NMR was performed, and is shown in Table 10. A TLC (silica gel, 50/50 Et$_2$O/hexanes, UV visualization) of the product, using the CDCl$_3$ solution was obtained, alongside a sample of the starting HMF ester. The approximate yield of acid was 41%. An analysis of the reaction is shown in Table 9.

An insoluble white solid was also isolated from the oxidation, which was not readily identifiable. This material remained on top of the filter aid used to filter the crude reaction mixture after adding chloroform. The solid was not soluble in chloroform nor in aqueous potassium hydroxide. An $^1$H-NMR spectrum was obtained on the filtered aqueous base extract, but no signals were observed above the background noise.

A melting point was determined on the crude product: softening at 68° C.; completely melted at 96° C. Considering that the material was a roughly 50:50 mixture with dimethylsulfone, the broad melting range was not unexpected. No decomposition was observed.

TABLE 9

Analysis of HMF ester oxidation reaction.

Components of Mixture

|  | CH$_3$CN | DMSO | sulfone | CMFA | CMF | CH$_2$Cl$_2$ | HMF ester | HMFA ester | Total Moles |
|---|---|---|---|---|---|---|---|---|---|
| Grams | 39.30 | 1.01 | 0 | 0 | 0.00 |  | 1.00 | 0.00 |  |
| MW | 96.10 | 78.13 | 94.13 | 160.56 | 144.56 | 84.93 | 308.41 | 324.41 |  |
| Moles | 0.4089 | 0.0129 | 0.0000 | 0.0000 | 0.0000 |  | 0.0032 | 0.0000 | 0.4219 |

TABLE 10

Analysis of product from HMF ester oxidation reaction.

| Products ($^1$H-NMR peak assignments) | Area | Molar Response | Proportional Weight | wt % | Sample Weight | % yield |
|---|---|---|---|---|---|---|
| CMFA (4.6 ppm) | 0.000 | 0.000 | 0.000 | 0.00 | 0.000 |  |
| acetonitrile (2.0 ppm) | 0.000 | 0.000 | 0.000 | 0.00 | 0.000 |  |
| dimethyl sulfoxide (2.8 ppm) | 26.889 | 4.482 | 0.350 | 9.68 | 0.107 | 10.6 |
| dimethylsulfone (3.0 ppm) | 107.333 | 17.889 | 1.684 | 46.54 | 0.517 | 42.4 |
| HMF ester (6.6 ppm) | 0.623 | 0.312 | 0.096 | 2.65 | 0.029 | 2.9 |
| HMFA ester (6.5 ppm) | 9.176 | 4.588 | 1.488 | 41.13 | 0.457 | 43.4 |
| methylene chloride (5.3 ppm) | 0.000 | 0.000 | 0.000 | 0.00 | 0.000 |  |
| Sums |  | 27.270 | 3.618 |  |  |  |

What is claimed is:

1. A method of producing a halomethylfuroic acid, or a salt thereof, comprising combining a halomethylfurfural, an organosulfur compound, and an oxidant to produce a halomethylfuroic acid, or a salt thereof,
wherein the oxidant is:
(i) a compound of formula $W^b$-O$_2$X$^b$, wherein $W^b$ is a Group I cation and $X^b$ is halo;
(ii) a compound of formula $W^d$-O$_3$X$^d$, wherein $W^d$ is a Group I cation and $X^d$ is halo;
(iii) a compound of formula HX$^b$O$_2$, wherein $X^b$ is halo;
(iv) a compound of formula HX$^d$O$_3$, wherein $X^d$ is halo; or
(v) a compound of formula X$^c$O$_2$, wherein $X^c$ is halo.

2. The method of claim 1, wherein the oxidant is HClO$_2$ or ClO$_2$.

3. The method of claim 1, wherein the organosulfur compound is dimethyl sulfoxide.

4. The method of claim 1, wherein the halomethylfurfural, the organosulfur compound and the oxidant are further combined with an acid.

5. The method of claim 4, wherein the acid is hydrochloric acid.

6. The method of claim 1, wherein the halomethylfurfural, the organosulfur compound and the oxidant are combined with water to form a reaction mixture, wherein the reaction mixture has a pH, and
wherein the method comprises adjusting the pH of the reaction mixture to a pH of between 0 and 5.

7. The method of claim 1, wherein the oxidant is a compound of formula $W^b$-O$_2$X$^b$, wherein $W^b$ is a Group I cation and $X^b$ is halo.

8. The method of claim 7, wherein $W^b$ is sodium, lithium or potassium.

9. The method of claim 7, wherein $X^b$ is chloro or bromo.

10. The method of claim 7, wherein the oxidant is sodium chlorite, lithium chlorite, potassium chlorite, or sodium bromite.

11. A method of producing a halomethylfuroic acid, or a salt thereof, comprising combining a halomethylfurfural and an oxidant to produce a halomethylfuroic acid, or a salt thereof, wherein the oxidant is a compound of formula $W^d$-O$_3$X$^d$, wherein $W^d$ is a Group I cation and $X^d$ is halo.

12. The method of claim 11, wherein $W^d$ is sodium, lithium or potassium.

13. The method of claim 11, wherein $X^d$ is chloro or bromo.

14. The method of claim 11, wherein the oxidant is sodium chlorate, potassium chlorate, lithium chlorate, or sodium bromate.

15. The method of claim 1, wherein the oxidant is a compound of formula HX$^b$O$_2$, wherein $X^b$ is halo.

16. The method of claim 15, wherein $X^b$ is chloro or bromo.

17. A method of producing a halomethylfuroic acid, or a salt thereof, comprising combining a halomethylfurfural and an oxidant to produce a halomethylfuroic acid, or a salt thereof, wherein the oxidant is a compound of formula HX$^d$O$_3$, wherein $X^d$ is halo.

18. The method of claim 17, wherein $X^d$ is chloro or bromo.

19. The method of claim 1, wherein the oxidant is a compound of formula X$^c$O$_2$, wherein $X^c$ is halo.

20. The method of claim 19, wherein $X^c$ is chloro or bromo.

21. The method of claim 1, wherein the halomethylfurfural is 5-chloromethylfurfural, and wherein the halomethylfuroic acid, or a salt thereof, is 5-chloromethyl-2-furoic acid, or a salt thereof.

22. The method of claim 1, wherein the halomethylfurfural, the organosulfur compound and the oxidant are further combined with water.

23. The method of claim 1, wherein the halomethylfuroic acid is produced at a yield of at least 50%.

24. The method of claim 1, wherein the halomethylfurfural the organosulfur compound and the oxidant are further combined with solvent.

25. The method of claim 24, wherein the solvent comprises an organic solvent.

26. The method of claim 25, wherein the solvent comprises acetic acid, dimethyl sulfoxide, dimethoxyethane, tetrahydrofuran, or acetonitrile, or any combinations thereof.

27. The method of claim 1, wherein the halomethylfurfural the organosulfur compound and the oxidant are further combined with an alkene, or a peroxide, or any combinations thereof.

28. The method of claim 1, wherein the halomethylfurfural the organosulfur compound and the oxidant are further combined with a buffer.

29. The method of claim 28, wherein the buffer is a phosphate buffer.

30. The method of claim 1, wherein the halomethylfurfural the organosulfur compound and the oxidant are further combined with an acid.

31. The method of claim 30, wherein the acid is hydrochloric acid.

32. The method of claim 1, wherein the mole ratio of the oxidant to the halomethylfurfural is between 0.1 and 4.0.

33. The method of claim 1, wherein the oxidant is chlorous acid or chlorine dioxide, further comprising:
producing hypochlorous acid from the chlorous acid or chlorine dioxide, and
removing the hypochlorous acid produced.

34. The method of claim 33, wherein the removing is performed with an alkene, or a peroxide, or any combinations thereof.

35. The method of claim 33, wherein less than 5 wt % of sodium hypochlorite is present relative to the oxidant.

36. The method of claim 1, wherein the oxidant is produced in situ.

37. The method of claim 1, wherein the oxidant is produced in situ from sodium halite and an acid.

38. The method of claim 1, further comprising isolating the halomethylfuroic acid, or a salt thereof, produced.

39. The method of claim 38, wherein the isolating comprises liquid-liquid extraction.

40. The method of claim 38, wherein the liquid-liquid extraction is performed with a haloalkyl solvent.

41. The method of claim 40, wherein the haloalkyl solvent comprises dichloromethane, chloroform, or dichloroethane, or any combinations thereof.

42. The method of claim 1, wherein less than 50% of the halomethyl group of the halomethylfurfural is hydrolyzed to a hydroxymethyl group.

43. The method of claim 1, wherein the halomethylfuroic acid, or a salt thereof, is a solid.

44. The method of claim 1, wherein the organosulfur compound is thiodiethanol.

45. The method of claim 11, wherein the halomethylfurfural and the oxidant are further combined with an organosulfur compound.

46. The method of claim 45, wherein the organosulfur compound is dimethyl sulfoxide.

47. The method of claim 45, wherein the organosulfur compound is dimethyl thiodiethanol.

48. The method of claim 17, wherein the halomethylfurfural and the oxidant are further combined with an organosulfur compound.

49. The method of claim 48, wherein the organosulfur compound is dimethyl sulfoxide.

50. The method of claim 48, wherein the organosulfur compound is dimethyl thiodiethanol.

* * * * *